US012796945B2

(12) United States Patent
Marks et al.

(10) Patent No.: US 12,796,945 B2
(45) Date of Patent: Nov. 17, 2026

(54) IMAGING PHOTOPLETHYSMOGRAPHY (IPPG) SYSTEM AND METHOD FOR REMOTE MEASUREMENTS OF VITAL SIGNS

(71) Applicant: Mitsubishi Electric Research Laboratories, Inc., Cambridge, MA (US)

(72) Inventors: Tim Marks, Cambridge, MA (US); Hassan Mansour, Cambridge, MA (US); Suhas Lohit, Cambridge, MA (US); Armand Comas Massague, Cambridge, MA (US); Xiaoming Liu, Cambridge, MA (US)

(73) Assignee: Mitsubishi Electric Research Laboratories, Inc., Cambridge, MA (US)

( * ) Notice: Subject to any disclaimer, the term of this patent is extended or adjusted under 35 U.S.C. 154(b) by 1153 days.

(21) Appl. No.: 17/486,981

(22) Filed: Sep. 28, 2021

(65) Prior Publication Data

US 2023/0063221 A1 Mar. 2, 2023

Related U.S. Application Data

(60) Provisional application No. 63/237,347, filed on Aug. 26, 2021.

(51) Int. Cl.
*A61B 5/024* (2006.01)
*A61B 5/00* (2006.01)
(Continued)

(52) U.S. Cl.
CPC ........ *A61B 5/02416* (2013.01); *A61B 5/0013* (2013.01); *A61B 5/0077* (2013.01);
(Continued)

(58) Field of Classification Search
CPC ... A61B 5/02416; A61B 5/7264; A61B 5/742; A61B 2576/00; G06T 7/0012; G06T 2207/20084; G06T 2207/30088
See application file for complete search history.

(56) References Cited

U.S. PATENT DOCUMENTS

| | | | | |
|---|---|---|---|---|
| 11,954,862 B2* | 4/2024 | Ren | ........................ | G16H 30/40 |
| 2018/0307927 A1* | 10/2018 | Hutchinson | ............ | G06V 20/46 |

(Continued)

OTHER PUBLICATIONS

X. Niu, S. Shan, H. Han and X. Chen, "Rhythm Net: End-to-End Heart Rate Estimation From Face via Spatial-Temporal Representation," in IEEE Transactions on Image Processing, vol. 29, pp. 2409-2423, 2020, [retrieved Oct. 7, 2024], Retrieved from [ https://ieeexplore.ieee.org/document/8879658] (Year: 2020).*

(Continued)

*Primary Examiner* — John Villecco
*Assistant Examiner* — Joshua B. Crockett
(74) *Attorney, Agent, or Firm* — Gene Vinokur

(57) ABSTRACT

An imaging photoplethysmography (iPPG) system is provided. The iPPG system receives a sequence of images of different regions of the skin of the person, where each region including pixels of different intensities indicative of variation of coloration of the skin. The iPPG system further transforms the sequence of images into a multidimensional time-series signal, each dimension corresponding to a different region from the different regions of the skin. The iPPG system further processes the multidimensional time-series signal with a time-series U-Net neural network wherein the pass-through layers include a recurrent neural network (RNN) to generate a PPG waveform, where the vital sign of the person is estimated based on the PPG waveform, and the iPPG system further renders the estimated vital sign of the person.

19 Claims, 18 Drawing Sheets

(51) Int. Cl.
*A61B 5/1171* (2016.01)
*G06T 7/00* (2017.01)

(52) U.S. Cl.
CPC ........ *A61B 5/02405* (2013.01); *A61B 5/1176* (2013.01); *A61B 5/7264* (2013.01); *A61B 5/742* (2013.01); *G06T 7/0012* (2013.01); *A61B 2576/00* (2013.01); *G06T 2207/20084* (2013.01); *G06T 2207/30088* (2013.01)

(56) References Cited

U.S. PATENT DOCUMENTS

| | | | | |
|---|---|---|---|---|
| 2020/0121256 | A1* | 4/2020 | Mcduff | A61B 5/0077 |
| 2021/0386307 | A1* | 12/2021 | Wu | A61B 5/725 |
| 2022/0156532 | A1* | 5/2022 | Paikin | G06V 10/803 |
| 2023/0196567 | A1* | 6/2023 | Aykut | G06N 3/0455 382/128 |
| 2023/0397826 | A1* | 12/2023 | Park | A61B 5/02416 |
| 2024/0041334 | A1* | 2/2024 | Devani | A61B 5/1128 |
| 2024/0395278 | A1* | 11/2024 | Serra | G10L 21/0216 |

OTHER PUBLICATIONS

Jo Schlemper, et al., "Attention gated networks: Learning to Leverage Salient Regions in Medical Images", Medical Image Analysis, vol. 53, pp. 197-207, ISSN 1361-8415, [retrieved Oct. 1, 2024], Retrieved from [https://www.sciencedirect.com/science/article/pii/S1361841518306133] (Year: 2019).*

Hsu YC, Li YH, Chang CC, Harfiya LN. Generalized Deep Neural Network Model for Cuffless Blood Pressure Estimation with Photoplethysmogram Signal Only. Sensors (Basel). Oct. 4, 2020;20(19):5668 [retrieved Oct. 1, 2024]. Retrieved from [https://www.ncbi.nlm.nih.gov/pmc/articles/PMC7582614/] (Year: 2020).*

S Hao, W Wang and M Salzmann, "Geometry-Aware Deep Recurrent Neural Networks for Hyperspectral Image Classification" in IEEE Transactions on Geoscience and Remote Sensing, vol. 59, No. 3, pp. 2448-2460, Mar. 2021 [retrieved Oct. 1, 2024]. Retrieved from [https://ieeexplore.ieee.org/document/9138475] (Year: 2021).*

Y Li, Y Liu and D S Williamson, "On Loss Functions for Deep-Learning Based T60 Estimation," IEEE International Conference on Acoustics, Speech and Signal Processing, Toronto, ON, Canada, 2021, pp. 486-490 [retrieved Oct. 1, 2024] retrieved from [https://ieeexplore.ieee.org/document/9414442?source=IQplus] (Year: 2021).*

MATLAB Answers post entitled "how to split channels of a video." 1 page, posted and answered on Apr. 24, 2019. Posted by user @Awais Khan and answered by user @KSSV. Retrieved from internet: [https://www.mathworks.com/matlabcentral/answers/458144-how-to-split-channels-of-a-video] (Year: 2019).*

MathWorks Help Center webpage entitled "Multidimensional Array." Oct. 1, 2024 Retrieved from Internet Archive [https://web.archive.org/web/20121110233243/https://www.mathworks.com/help/matlab/math/multidimensional-arrays.html] (Year: 2012).*

MathWorks Help Center webpage entitled "cell." Oct. 6, 2020. Retrieved from [https://web.archive.org/web/20201006131708/https://www.mathworks.com/help/matlab/ref/cell.html] (Year: 2020).*

MathWorks Help Center webpage entitled "imapplymatrix." Feb. 7, 2018. Retrieved from [https://web.archive.org/web/20180207204659/https://www.mathworks.com/help/images/ref/imapplymatrix.html] (Year: 2018).*

A Comas, et. al. "Turnip: Time-Series U-Net With Recurrence for NIR Imaging PPG," 2021 IEEE International Conference on Image Processing, Anchorage, AK, USA, 2021, pp. 309-313, doi: 10.1109/ICIP42928.2021.9506663. Retrieved from [https://ieeexplore.ieee.org/document/9506663?source=IQplus] on Oct. 7, 2024 (Year: 2021).*

Alom et al., "Recurrent Residual Convolutional Neural Network based on U-Net (R2U-Net) for Medical Image Segmentation", arXiv.org, publ. May 29, 2018. Accessed via <https://arxiv.org/abs/1802.06955> on Mar. 6, 2025. (Year: 2018).*

Hu et al. "Retinal Vessel Segmentation Based on Recurrent Convolutional Skip Connection U-Net," 2021 4th International Conference on Intelligent Autonomous Systems (ICoIAS), Wuhan, China, 2021, pp. 65-71. Accessed Aug. 5, 2025 via <https://ieeexplore.ieee.org/xpl/conhome/9527534/proceeding> (Year: 2021).*

Comas et al. "Turnip: Time-Series U-Net With Recurrence For NIR Imaging PPG," 2021 IEEE International Conference on Image Processing (ICIP), Anchorage, AK, USA, 2021, pp. 309-313, publ. on IEEE Xplore Aug. 23, 2021, accessed Dec. 1, 2025 via <https://ieeexplore.ieee.org/document/9506663> (Year: 2021).*

Azad et al., "Bi-Directional ConvLSTM U-Net with Densley Connected Convolutions," 2019 IEEE/CVF International Conference on Computer Vision Workshop (ICCVW), Seoul, Korea (South), 2019, pp. 406-415, accessed Dec. 2, 2025 via <https://ieeexplore.ieee.org/document/9022282> (Year: 2019).*

"Working with Documents—Publication Dates", IEEE Xplore, accessed Feb. 28, 2026 via <https://ieeexplore.ieee.org/Xplorehelp/ieee-xplore-training/working-with-documents#publication-dates> (Year: 2026).*

Alom et al. "Recurrent Residual UNet for MEdical Image Segmentation," Journal of Medical Imaging. Medicalimaging.spiedigitallibrary.org. 6(1), 014006 (Jan-Mar. 2019).

* cited by examiner

IMAGING PHOTOPLETHYSMOGRAPHY (IPPG) SYSTEM AND METHOD FOR REMOTE MEASUREMENTS OF VITAL SIGNS

TECHNICAL FIELD

The present disclosure relates generally to remotely monitoring vital signs of a person and more particularly to an imaging photoplethysmography (iPPG) system and a method for remote measurements of vital signs.

BACKGROUND

Vital signs of a person, for example heart rate (HR), heart rate variability (HRV), respiration rate (RR), or blood oxygen saturation, serve as indicators of a person's current state and as a potential predictor of serious medical events. For this reason, vital signs are extensively monitored in inpatient and outpatient care settings, at home, and in other health, leisure, and fitness settings. One way of measuring the vital signs is plethysmography. Plethysmography corresponds to measurement of volume changes of an organ or a body part of a person. There are various implementations of Plethysmography, such as Photoplethysmography (PPG).

PPG is an optical measurement technique that evaluates a time-variant change of light reflectance or transmission of an area or volume of interest, which can be used to detect blood volume changes in microvascular bed of tissue. PPG is based on a principle that blood absorbs and reflects light differently than surrounding tissue, so variations in the blood volume with every heartbeat affect light transmission or reflectance correspondingly. PPG is often used non-invasively to make measurements at the skin surface. The PPG waveform includes a pulsatile physiological waveform attributed to cardiac-synchronous changes in the blood volume with each heartbeat and is superimposed on a slowly varying baseline with various lower frequency components attributed to other factors such as respiration, sympathetic nervous system activity, and thermoregulation.

Conventional pulse oximeters, for measuring the heart rate and the (arterial) blood oxygen saturation of a person, are attached to the skin of the person, for instance to a fingertip, earlobe, or forehead. Therefore, they are referred to as 'contact' PPG devices. A typical pulse oximeter can include a combination of a green LED, a blue LED, a red LED, and an infrared LED as light sources and one photodiode for detecting light that has been transmitted through patient tissue. Conventional available pulse oximeters quickly switch between measurements at different wavelengths and thereby measure transmissivity of the same area or volume of tissue at different wavelengths. This is referred to as time-division-multiplexing. The transmissivity over time at each wavelength yields the PPG signals for different wavelengths. Although contact PPG is regarded as a basically non-invasive technique, contact PPG measurement is often experienced as being unpleasant, since the pulse oximeter is directly attached to the person and any cables limit freedom to move.

Recently, non-contact, remote PPG (RPPG) for unobtrusive measurements has been introduced. RPPG utilizes light sources or, in general, radiation sources disposed remotely from the person of interest. Similarly, a detector, e.g., a camera or a photo detector, can be disposed remotely from the person of interest. RPPG is also often referred to as imaging PPG (iPPG), due to its use of imaging sensors such as cameras. (Hereinafter, the terms remote PPG (RPPG) and imaging PPG (iPPG) are used interchangeably.) Because they do not require direct contact with a person, remote photoplethysmography systems and devices are considered unobtrusive and are in that sense well suited for medical as well as non-medical everyday applications.

One advantage of camera-based vital signs monitoring versus on-body sensors is ease of use. There is no need to attach a sensor to the person, as aiming the camera at the person is sufficient. Another advantage of camera-based vital signs monitoring over on-body sensors is that cameras have greater spatial resolution than contact sensors, which mostly include a single-element detector.

One of the challenges for RPPG technology is to be able to provide accurate measurements in a volatile environment where there exist unique sources of noise. For example, in a volatile environment such as in-vehicle environment, illumination on a driver varies drastically and suddenly during driving (e.g., while driving through shadows of buildings, trees, etc.), making it difficult to distinguish iPPG signals from other variations. Also, there is significant motion of the driver's head and face due to a number of factors, such as motion of the vehicle, the driver looking around both within and outside the car (for oncoming traffic, looking into rear-view mirrors and side-view mirrors), and the like.

Several methods have been developed to enable robust camera-based vital signs measurement. One of these methods uses a narrow-band active near-infrared (NIR) illumination, where the NIR illumination greatly reduces the adverse effects of lighting variation. During driving, for example, this method can reduce adverse effects of lighting variation such as sudden variation between sunlight and shadow, or passing through streetlights and other cars' headlights, without impacting the driver's ability to see at night. However, NIR frequencies introduce new challenges for iPPG, including low signal-to-noise ratio (SNR). Reasons for this include that in the NIR portion of the spectrum, camera sensors have reduced sensitivity, and blood-flow related intensity changes have smaller magnitude. Accordingly, there is a need for a RPPG system which can accurately estimate PPG signals from the NIR frequencies.

SUMMARY

Accordingly, it is an object of some embodiments to estimate vital signs of a person with high accuracy. To that end, some embodiments utilize imaging photoplethysmography (iPPG). It is also an objective of some embodiments to use a narrow-band near-infrared (NIR) system and determine a wavelength range that reduces illumination variations. Additionally or alternatively, some embodiments aim to use NIR monochromatic videos (or a sequence of images) to obtain multidimensional time-series data associated with different regions of a skin of the person and accurately estimate the vital signs of the person by processing the multidimensional time-series data using a deep neural network (DNN).

Some embodiments are based on the realization that the vital signs of the person can be estimated from NIR monochromatic video or a sequence of NIR images. To that end, the iPPG system obtains a sequence of NIR images of a face of a person of interest (also referred to as "person") and partitions each image into a plurality of spatial regions. Each spatial region comprises a small portion of the face of the person. The iPPG system analyses variation in skin color or intensity in each region of the plurality of spatial regions to estimate the vital signs of the person.

To that end, the iPPG system generates a multidimensional time-series signal, wherein the dimensions of the multidimensional signal at each time instant correspond to the number of spatial regions, and each time point corresponds to one image in the sequence of images. The multidimensional time-series signal is then provided to a deep neural network (DNN)-based module to estimate the vital signs of the person. The DNN-based module applies a time-series U-Net architecture to the multidimensional time-series data, wherein the pass-through connections of the U-Net architecture are modified to incorporate temporal recurrence for NIR imaging PPG.

Some embodiments are based on the realization that the usage of a recurrent neural network (RNN) in pass-through layers of the U-Net neural network to sequentially process the multidimensional time-series signal can enable more accurate estimation of the vital signs of the person.

Some embodiments are based on recognition that sensitivity of PPG signals to noise in measurements of intensities (e.g., pixel intensities in NIR images) of a skin of a person is caused at least in part by independent estimation of photoplethysmographic (PPG) signals from the intensities of a skin of a person measured at different spatial positions (or spatial regions). Some embodiments are based on recognition that at different locations, e.g., at different regions of the skin of the person, the measurement intensities can be subjected to different measurement noise. When the iPPG signals are independently estimated from intensities at each location (e.g., the PPG signal estimated from intensities at one skin region is estimated independently of the intensities or estimated signals from other skin regions), the independence of the different estimates may cause an estimator to fail to identify such noise.

Some embodiments are based on recognition that measured intensities at different spatial regions of the skin of the person can be subjected to different and sometimes even unrelated noise. The noise includes one or more of illumination variations, motion of the person, and the like. In contrast, heartbeat is a common source of intensity variations present in the different regions of the skin. Thus, the effect of the noise on the quality of the vital signs' estimation can be reduced when the independent estimation is replaced by a joint estimation of PPG signals measured from the intensities at different regions of the skin of the person. In this way, some embodiments can extract the PPG signal that is common to many skin regions (including regions that may also contain considerable noise), while ignoring noise signals that are not shared across many skin regions.

Some embodiments are based on recognition that it can be beneficial to estimate the PPG signals of the different skin regions collectively, because by estimating the PPG signal of the different skin regions collectively, noise affecting the estimation of the vital signs is reduced. Some embodiments are based on recognition that two types of noise are acting on the intensities of the skin, i.e., external noise and internal noise. The external noise affects the intensity of the skin due to external factors such as lighting variations, motion of the person, and resolution of the sensor measuring the intensities. The internal noise affects the intensity of the skin due to internal factors such as different effects of cardiovascular blood flow on appearance of different regions of the skin of the person. For example, the heartbeat can affect the intensity of the forehead and cheeks of the person more than it affects the intensity of the nose.

Some embodiments are based on realization that both types of noise can be addressed in the frequency domain of the intensity measurements. Specifically, the external noise is often non-periodic or has a periodic frequency different than that of a signal of interest (e.g., pulsatile signal), and thus can be detected in the frequency domain. On the other hand, the internal noise, while resulting in intensity variations or time-shifts of the intensity variations in different regions of the skin, preserves the periodicity of the common source of the intensity variations in the frequency domain.

Some embodiments aim to provide accurate estimation of the vital signs even in volatile environments where there is dramatic illumination variation. For example, in a volatile environment such as an in-vehicle environment, some embodiments provide an RPPG system suitable for estimating vital signs of a driver or passenger of a vehicle. However, during driving, illumination on a person's face can change dramatically. To address these challenges, additionally or alternatively one embodiment uses active in-car illumination, in a narrow spectral band in which the sunlight, streetlamp, and headlight and taillight spectral energy are all minimal. For example, due to the water in the atmosphere, the sunlight that reaches the earth's surface has much less energy around the NIR wavelength of 940 nm than it does at other wavelengths. The light output by streetlamps and vehicle lights is typically in the visible spectrum, with very little power at infrared frequencies. To that end, one embodiment uses an active narrow-band illumination source at or near 940 nm and a camera filter at the same frequency, which ensures that the illumination changes due to environmental ambient illumination are filtered away. Further, since this narrow frequency band is beyond the visible range, humans do not perceive this light source and thus are not distracted by its presence. Moreover, the narrower the bandwidth of the light source used in the active illumination, the narrower the bandpass filter on the camera can be, which further rejects intensity changes due to ambient illumination.

Accordingly, one embodiment uses a narrow-bandwidth (narrow-band) near-infrared (NIR) light source to illuminate the skin of the person at a narrow frequency band including a near-infrared wavelength of 940 nm and an NIR camera with a narrow-band filter overlapping the wavelengths of the narrow-band light source to measure the intensities of different regions of the skin in the narrow frequency band.

One embodiment discloses an imaging photoplethysmography (iPPG) system for estimating a vital sign of a person from images of a skin of the person, comprising: at least one processor; and memory having instructions stored thereon that, when executed by the at least one processor, cause the iPPG system to: receive a sequence of images of different regions of the skin of the person, each region including pixels of different intensities indicative of variation of coloration of the skin; transform the sequence of images into a multidimensional time-series signal, each dimension corresponding to a different region from the different regions of the skin; process the multidimensional time-series signal with a time-series U-Net neural network to generate a PPG waveform, wherein a U-shape of the time-series U-Net neural network includes a contracting path formed by a sequence of contractive layers followed by an expansive path formed by a sequence of expansive layers, wherein at least some of the contractive layers downsample their input and at least some of the expansive layers upsample their input, forming pairs of contractive and expansive layers of corresponding resolutions wherein at least some of the corresponding contractive layers and expansive layers are connected through pass-through layers. Further, at least one of the pass-through layers includes a recurrent neural network that processes its input sequentially. The at least one processor is further configured to estimate the vital sign of the person based on the PPG waveform and render the estimated vital sign of the person.

Another embodiment discloses a method for estimating a vital sign of a person, the method comprising: receiving a sequence of images of different regions of the skin of the person, each region including pixels of different intensities indicative of variation of coloration of the skin; transforming the sequence of images into a multidimensional time-series signal, each dimension corresponding to a different region from the different regions of the skin; processing the multidimensional time-series signal with a time-series U-Net neural network to generate a PPG waveform, wherein a U-shape of the time-series U-Net neural network includes a contracting path formed by a sequence of contractive layers followed by an expansive path formed by a sequence of expansive layers, wherein at least some of the contractive layers down sample their input and at least some of the expansive layers up sample their input forming pairs of contractive and expansive layers of corresponding resolutions, wherein at least some of the corresponding contractive layers and expansive layers are connected through pass-through layers, and wherein each of the pass-through layers includes a recurrent neural network that processes its input sequentially. The method further comprises estimating the vital sign of the person based on the PPG waveform and rendering the estimated vital sign of the person.

BRIEF DESCRIPTION OF THE DRAWINGS

FIG. 1I illustrates steps of a method executed by the iPPG system using color video, according to an example embodiment.

DETAILED DESCRIPTION

In the following description, for purposes of explanation, numerous specific details are set forth in order to provide a thorough understanding of the present disclosure. It will be apparent, however, to one skilled in the art that the present disclosure may be practiced without these specific details. In other instances, apparatuses and methods are shown in block diagram form only in order to avoid obscuring the present disclosure.

As used in this specification and claims, the terms "for example," "for instance," and "such as," and the verbs "comprising," "having," "including," and their other verb forms, when used in conjunction with a listing of one or more components or other items, are each to be construed as open ended, meaning that that the listing is not to be considered as excluding other, additional components or items. The term "based on" means at least partially based on. Further, it is to be understood that the phraseology and terminology employed herein are for the purpose of the description and should not be regarded as limiting. Any heading utilized within this description is for convenience only and has no legal or limiting effect.

Figure 1A:
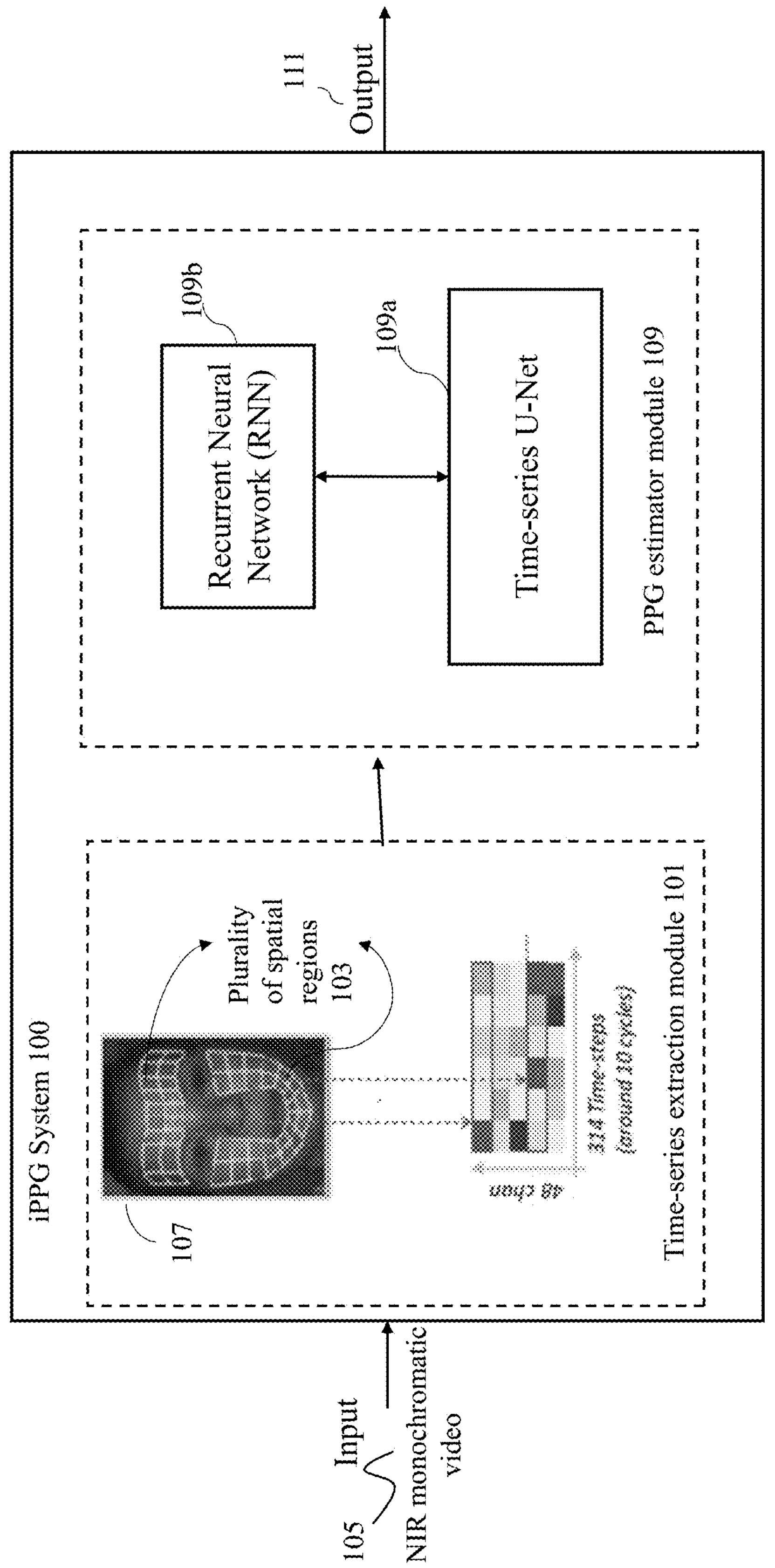
FIG. 1A shows a block diagram illustrating an imaging photoplethysmography (iPPG) system for estimating a vital sign of a person from near-infrared (NIR) video, according to an example embodiment.

FIG. 1A shows a block diagram illustrating an imaging photoplethysmography (iPPG) system 100 for estimating a vital sign of a person, according to an example embodiment. The iPPG system 100 corresponds to a modular framework, where a time-series extraction module 101 and a PPG estimator module 109 may be used to generate a PPG waveform (also referred to as "PPG signal") from input images of different regions of a skin of a person. The PPG waveform may be further used to accurately estimate one or more vital signs of the person. In some embodiments, one or both of the time-series extraction module 101 and the PPG estimator module 109 may be implemented using a neural network.

In some embodiments, the iPPG system 100 may include a near-infrared (NIR) light source configured to illuminate the skin of the person, and a camera configured to capture a monochromatic video 105 (also referred as the NIR video 105). The NIR video 105 captures at least one body part of one or more persons (such as a face of a person). For ease of explanation, assume that the NIR video 105 captures the face of the person. The NIR video 105 includes a plurality of frames. Therefore, each frame in the NIR video 105 comprises an image 107 of the face of the person. In operation, the iPPG system 100 obtains input(s) such as the NIR video 105. In some embodiments, the image 107 in each frame of the NIR video 105 is partitioned into a plurality of spatial regions 103, where the plurality of spatial regions 103 is analyzed jointly to accurately determine the PPG waveform.

Figure 1B:
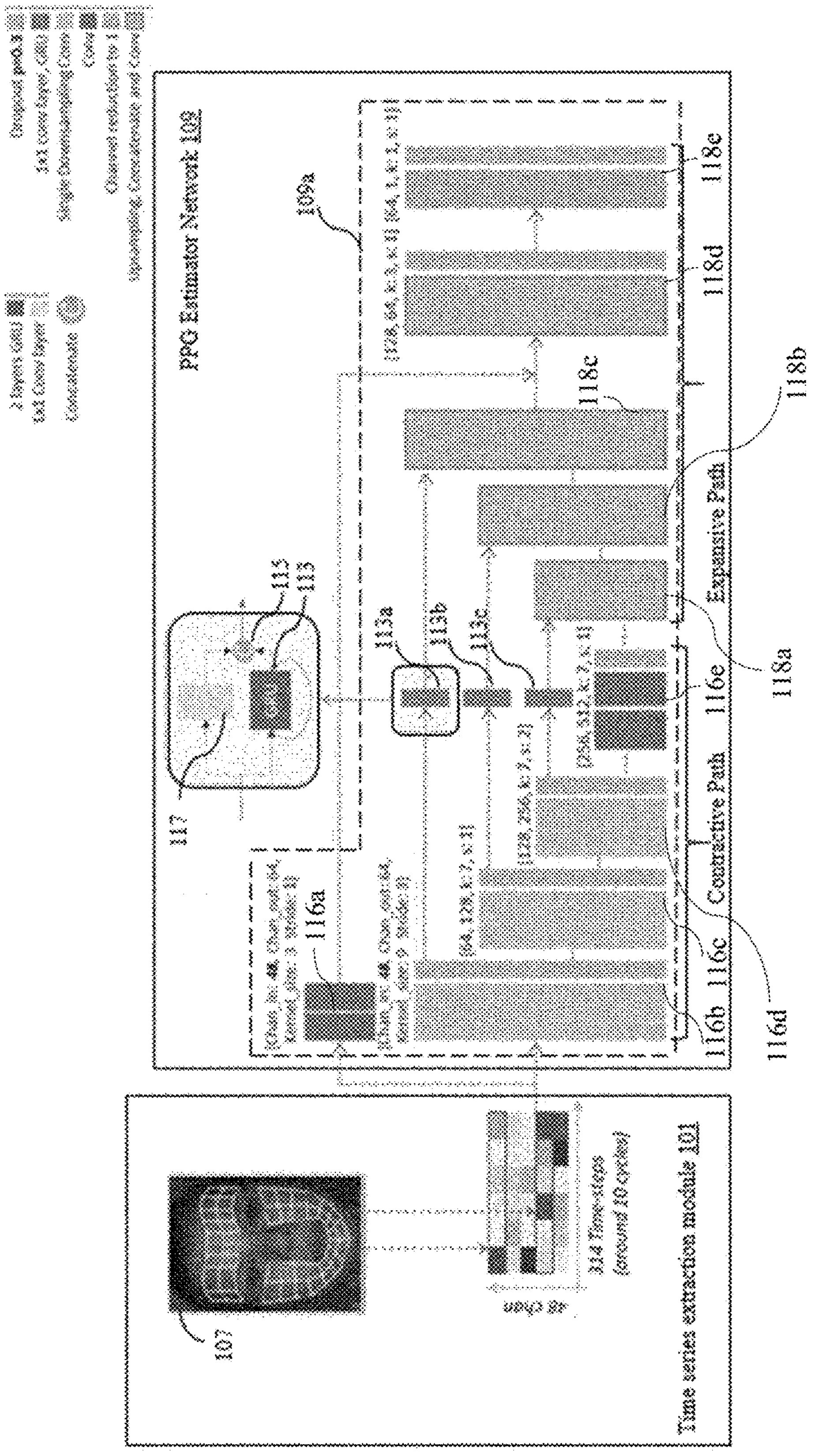
FIG. 1B illustrates a functional diagram of iPPG system, according to an example embodiment.
Figure 1C:
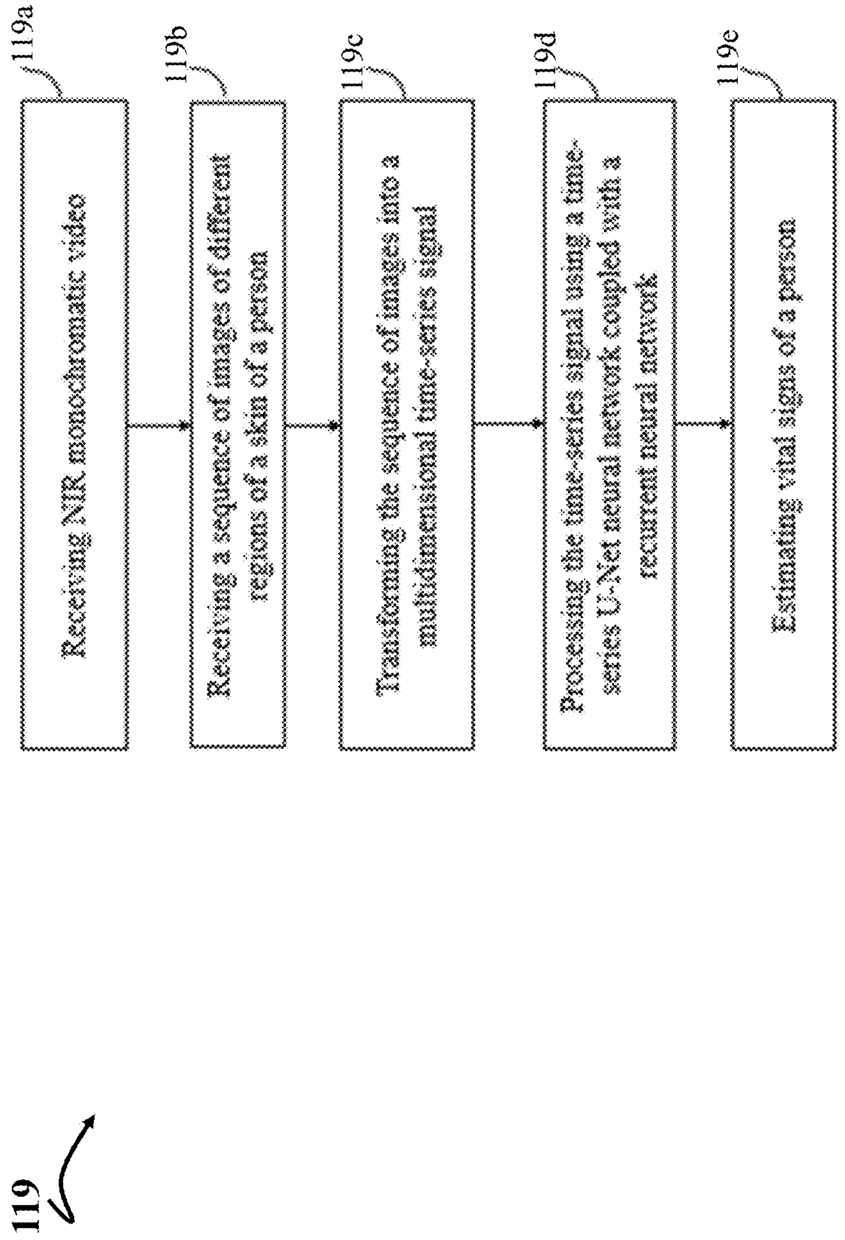
FIG. 1C illustrates steps of a method executed by the iPPG system using NIR video, according to an example embodiment.
Figure 1D:
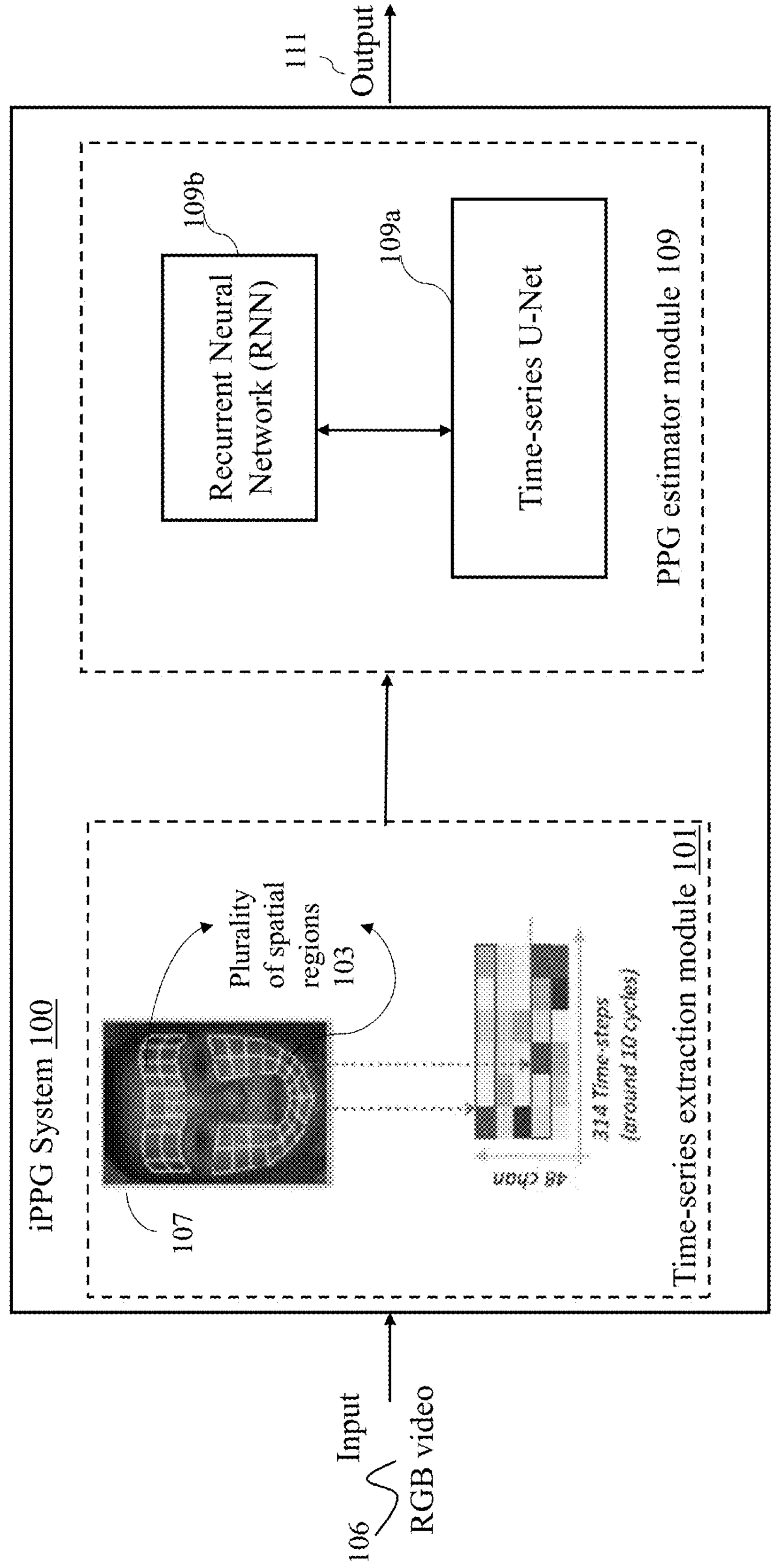
FIG. 1D shows a block diagram illustrating an imaging photoplethysmography (iPPG) system for estimating a vital sign of a person from color video, according to an example embodiment.

FIG. 1D shows a block diagram illustrating an alternative embodiment in which the iPPG system 100 may include a color camera to capture a color video such as an RGB video 106 (which is so called because it contains red (R), green (G), and blue (B) color channels). The RGB video 106 captures at least one body part of one or more persons (such as a face of a person).

For ease of explanation, assume that the RGB video 106 captures the face of the person. The RGB video 106 includes a plurality of frames. Therefore, each frame in the RGB video 106 comprises an image 107 of the face of the person. In this embodiment (unlike the embodiment pictured in FIG. 1C), the image 107 is an RGB image. In operation, the iPPG system 100 obtains input(s) such as the RGB video 106. In some embodiments, the RGB image 108 in each frame of the RGB video is split into the red (R), green (G) and blue (B) channels. Each channel is partitioned into a plurality of spatial regions 103, where the plurality of spatial regions 103 is analyzed jointly to accurately determine the PPG waveform. In some preferred embodiments, the pixel locations corresponding to each spatial region are consistent across the color channels.

The partitioning (segmentation) of each image 107 is based on the realization that specific areas of the body part under consideration contain the strongest PPG signal. For example, specific areas of a face (also referred to as "regions of interest (ROIs)," also referred to as simply "regions") containing the strongest PPG signals include areas located around forehead, cheeks, and chin (as shown in FIG. 1A). Accordingly, the image segmentation may be performed by using at least one image segmentation technique such as segmentation based on estimated face landmark locations, semantic segmentation, face parsing, thresholding segmentation, edge-based segmentation, region-based segmentation, watershed segmentation, clustering-based segmentation algorithms, and neural networks for segmentation.

The partitioning of each image 107 results in a sequence of images comprising different spatial regions of the plurality of spatial regions 103, where each spatial region includes a different part of the skin of the person. For example, in the NIR video 105 and the RGB video 106 of the face of the person, the image 107 in each frame of the video corresponds to the face of the person, and the plurality of spatial regions 103 in the sequence of images formed by partitioning the image 107 into the may correspond to areas of the skin of the person. Further, each spatial region of the plurality of spatial regions 103 is used to determine PPG signal. Due to occlusions of parts of the face, which may be due to one or more occluders such as hair (such as bangs over the forehead), facial hair, an object (such as sunglasses), another body part (such as a hand), and head pose or camera pose causing part of the face to not be visible in the image, some regions may not contain skin or may only partially contain skin, which may disrupt or weaken the quality of the signal from those regions.

Some embodiments are based on recognition that sensitivity of PPG signals to noise in measurements of intensities (e.g., pixel intensities in images) of a skin of a person is caused at least in part by independent estimation of PPG signals from the intensities of a skin of a person measured at different spatial positions (or spatial regions). Some embodiments are further based on recognition that at different locations, e.g., at different regions of the skin of the person, the measurement intensities can be subjected to different measurement noise. When the PPG signals are independently estimated from intensities at each spatial region (e.g., the PPG signal estimated from intensities at one skin region is estimated independently of the intensities or estimated signals from other skin regions), the independence of the different estimates may cause an estimator to fail to identify such noise affecting accuracy in determining the PPG signal.

The noise may be due to one or more of illumination variations, motion of the person, and the like. Some embodiments are based on further realization that heartbeat is a common source of the intensity variations present in the different regions of the skin. Thus, the effect of the noise on the quality of vital signs' estimation can be reduced when the independent estimation is replaced by a joint estimation of PPG signals measured from the intensities at different regions of the skin of the person.

Therefore, the iPPG system 100 jointly analyzes the plurality of spatial regions 103 in order to estimate the vital sign to reduce the effect of noise, where the vital sign is one or a combination of pulse rate of the person, and a heart rate variability (also referred to as "heartbeat signal") of the person. In some embodiments, the vital sign of the person is a one-dimensional signal at each time instant in a time series.

Some embodiments are based on the realization that the vital sign may be estimated accurately by adopting temporal analysis. Therefore, the iPPG system 100 is configured to extract at least one multidimension time-series signal from the sequence of images corresponding to different regions of the skin of the person, where the time-series signal is used to determine the PPG signal to accurately estimate the vital sign.

To that end, the iPPG system 100 uses the time-series extraction module 101.

Time-Series Extraction Module:

In some embodiments, the time-series extraction module 101 is configured to receive a sequence of images of a plurality of frames of the NIR video 105 and to extract the multidimensional time-series signal from the sequences of images. In some embodiments, the time-series extraction module 101 is further configured to partition the image 107 from a frame of the NIR monochromatic video 105 into the plurality of spatial regions 103 and generate a multidimensional time series corresponding to the plurality of spatial regions 103.

In other embodiments, the time-series extraction module 101 is configured to receive a sequence of images of a plurality of frames of the RGB video 106 and to extract the multidimensional time-series signal from the sequences of images. In some embodiments, the time-series extraction module 101 is further configured to partition the image 107 from a frame of the RGB video 106 into red (R), green (G) and blue (B) channels. In some embodiments, the timeseries extraction module 101 is further configured to partition each of R, G, and B channels of the image into a plurality of spatial regions 103 and generate multidimensional time series corresponding to the plurality of spatial regions 103.

The images 107 in the sequence of images may contain different regions of a skin of the person, where each region includes pixels of different intensities indicative of variation of coloration of the skin. FIG. 1A shows skin regions that are located on the face (facial regions), but it is understood that various embodiments are not limited to using the face. In some embodiments, the sequence of images corresponding to other regions of exposed skin, such as the person's neck or wrists, may be obtained and processed by the time-series extraction module 101.

In some embodiments, each dimension of the multidimensional time-series signal obtained from the NIR monochromatic video 105 corresponds to a different spatial region from the plurality of spatial regions of skin of the person in the image 107.

In some embodiments, each dimension of the multidimensional time-series signal obtained from the RGB video 106 corresponds to a different color channel and a different spatial region from the plurality of spatial regions of skin of the person in the image 107.

Further, in some embodiments, each dimension is a signal from an explicitly tracked (alternatively, explicitly detected in each frame) region of interest (ROI) of the plurality of spatial regions of the skin of the person. The tracking (alternatively, the detection) reduces an amount of motion-related noise. However, the multidimensional time-series still contains significant noise due to factors such as landmark localization errors, lighting variations, 3D head rotations, and deformations such as facial expressions.

To recover a signal of interest (PPG signal) from the noisy multidimensional time-series signal, the multidimensional time-series signal is given to the PPG estimator module 109.

PPG Estimator Module:

The PPG estimator module 109 is configured to recover and output 111 the PPG signal from the noisy multidimensional time-series signal. Further, based on the PPG signal, the vital signs of the person are determined.

Given the semi-periodic nature of the time-series signal obtained by the PPG estimator module 109, architecture of the PPG estimator module 109 is designed to extract temporal features at different time resolutions. To that end, the PPG estimator module 109 is implemented using a neural network such as a recurrent neural network (RNN), a deep neural network (DNN), and the like.

In some embodiments, the present disclosure proposes a Time-series U-net with Recurrence for Imaging PPG (TURNIP) architecture for the PPG estimator module 109. FIG. 1B illustrates the TURNIP architecture, which is based on a U-net architecture coupled with an RNN architecture.

Some embodiments are based on realization that the U-net is a convolutional network architecture, which has been used in image processing applications such as image segmentation. The U-net architecture is a "U" shaped architecture, where the U-net architecture includes contracting path on a left side of the U-net architecture and an expansive path on a right side of the U-net architecture. The U-Net architecture can be broadly categorized into an encoder network that corresponds to the contracting path, and a decoder network that corresponds to the expansive path, where the encoder network is followed by the decoder network.

The encoder network forms a first half of the U-net architecture. In the image processing applications in which the U-net architecture is typically used, the encoder is comprised of a series of spatial convolutional layers and may have max-pooling downsampling layers to encode the input image into feature representations at multiple different levels.

The decoder network forms a second half of the U-net architecture and comprises a series of convolutional layers as well as upsampling layers. The goal of the decoder network is to semantically project the (lower resolution) features learned by the encoder network back into the original (higher resolution) space. In the image processing applications in which the U-net architecture is typically used, the convolutional layers use spatial convolutions, and the input and output space are image pixel spaces.

Some embodiments are based on the realization that the input of the PPG estimator module 109 (also referred to as the "PPG estimator network") is a multidimensional time series, and the desired output is a one-dimensional time series of the vital sign. Accordingly, in some preferred embodiments, the convolutional layers of the encoder and decoder subnetworks of the time-series U-net 109*a* use temporal convolutions.

Some embodiments are based on further realization that the recurrent neural network (RNN) is a class of artificial neural networks (ANNs) where connections between nodes form a directed graph along a temporal sequence. The directed graph allows the RNN to exhibit temporal dynamic behavior. Unlike feedforward neural networks, RNNs can use their internal state (memory) to process variable length sequences of inputs. Accordingly, RNN's are capable of remembering important features of past inputs, which allows the RNN to more accurately determine temporal patterns. Therefore, the RNN can form a much deeper understanding of a sequence and its context. Hence, the RNN can be used for sequential data such as time series.

In some embodiments of the proposed TURNIP architecture of the iPPG system 100, a U-Net architecture is applied to the time series data. In some embodiments, the pass-through connections incorporate 1×1 convolutions. Unlike in previous U-Nets, in TURNIP the pass-through connections are modified to incorporate temporal recurrence by using an RNN. Thus, the PPG estimator module 109 comprises a time-series U-Net neural network (also referred to as "U-net") 109*a* coupled with a recurrent neural network (RNN) 109*b*. The U-net 109*a* and the RNN 109*b* are coupled to process the multidimensional time-series data to accurately determine the PPG waveform, where the PPG waveform is used to estimate the vital sign of the person. More details regarding the workings of the proposed iPPG system 100 using the TURNIP architecture is described below in more detail with reference to FIGS. 1B-1J.

FIG. 1B illustrates a functional diagram of the iPPG system 100, according to an example embodiment. FIG. 1B is described in conjunction with FIG. 1A. The iPPG system 100 initially receives one or more videos of a body part (for example, a face) of a person. The one or more videos may be near-infrared (NIR) videos. In some embodiments, the iPPG system 100 comprises an NIR illumination source and a camera, where the NIR illumination is configured to illuminate the body part of the person with NIR light so that the camera can record one or more NIR videos of the specific body part of the person. The one or more NIR videos are used to determine PPG waveform using the TURNIP architecture.

To that end, the iPPG system 100, for each NIR video 105 of the one or more videos, obtains an image (for example, image 107) from each of a sequence of image frames of the NIR video 105. Each image is partitioned or segmented into a plurality of spatial regions (for example, the spatial regions 103), resulting in a sequence of images whose spatial regions corresponding to different areas of the body part. The partitioning of the image 107 is performed such that each spatial region comprises a specific area of the body part that may be strongly indicative of the PPG signal. Thus, each spatial region of the plurality of spatial regions 103 is a region of interest (ROI) for determining PPG signal. Further, for each of the spatial region a time-series signal is derived using the time-series extraction module 101.

In an example embodiment, for each NIR video 105, the time-series extraction module 101 extracts a 48-dimensional time series corresponding to pixel intensities over time of 48 facial regions (ROIs), where the facial regions correspond to the plurality of spatial regions 103. In some embodiments, the multidimensional time series signal may have more or less than 48 dimensions corresponding to more or less than 48 facial regions.

In some embodiments, to extract the ROIs associated with a specific body part of the person in the image, a plurality of landmarks locations corresponding to the specific body part of the persons is localized in each image frame 107 of the video. Therefore, the plurality of landmark locations may vary depending on the body part used for PPG signal determination. In an example embodiment, when the face of the person is used for determining the PPG signal, 68 landmark locations corresponding to the face of the person (i.e., 68 facial landmarks) are localized in each image frame 107 of the video.

Some embodiments are based on the realization that due to imperfect or inconsistent landmark localization, motion jitter of estimated landmark locations in subsequent frames causes the boundaries of regions to jitter from one frame to the next, which adds noise to the extracted time series. To lessen the degree of this noise, the plurality of landmark locations are temporally smoothed prior to extracting the ROIs (e.g., the 48 facial regions).

Therefore, in some embodiments, before extracting the ROI from the plurality of landmark locations, the plurality of landmark locations are smoothed across time using a smoothing technique such as a moving average technique. In particular, a temporal kernel of a predetermined length is applied to the plurality of landmark locations over time to determine each landmark's location in each video frame image 107 as a weighted average of the estimated locations of the landmark in the preceding frames and subsequent frames within a time window corresponding to the length of the kernel.

For instance, in one embodiment, 68 landmark locations are smoothed using the moving average with a kernel of length 11 frames. The smoothed landmark locations in each frame of the NIR video 105 (that is, in each image 107) are then used to extract the 48 ROIs located around the forehead, cheeks, and chin in the frame. Then, the average intensity of the pixels in each spatial region of the 48 spatial regions is computed for the frame. In this way, an intensity value for each region in the plurality of spatial regions 103 (or ROIs) is extracted from each image, where the intensity values from the plurality of spatial regions 103 for a sequence of frames 107 (e.g., a sequence of 314 frames) forms a multidimensional time series.

The time-series extraction module 101 is configured to transform the sequence of images 107 corresponding to the plurality of spatial regions 103 into the multidimensional time series signal. Some embodiments are based on a realization that spatial averaging reduces the impact of sources of noise, such as quantization noise of a camera that captured the video the NIR video 105 or the RGB video 106 and minor deformations due to head and face motion of the person. To that end, pixel intensities of pixels from each spatial region of the plurality of spatial regions (also referred to as "different spatial regions") 103 at an instant of time are averaged to produce a value for each dimension of the multidimensional time-series signal at the instant of time.

In some embodiments, the time-series extraction module 101 is further configured to temporally window (or segment) the multidimensional time series signals. Accordingly, there may be a plurality of segments of the multidimensional time-series signals, where at least some part of each segment of the plurality of segments overlaps with a subsequent segment of the plurality of segments forming a sequence of overlapping segments. Further, the multidimensional time series corresponding to each of the segments is normalized before submitting the multidimensional time series signals to the PPG estimator module 109, where the PPG estimator module 109 may process, using the time-series U-Net 109*a*, each segment from the sequence of overlapping of the multidimensional time-series signals.

The windowed sequences are of specific duration with a specific frame stride during inference (e.g., 10 seconds duration (300 frames at 30 fps) with a 10-frame stride during inference), where stride indicates a number of frames (e.g., 10 frames) temporal shift between subsequent windowed sequences (e.g., the 10-second windowed sequences).

In an example case where the vital sign to be estimated for the person is a heartbeat signal, the heartbeat signal is locally periodic, where a period of the heartbeat signal changes over time. In such a case, some embodiments are based on realization that the 10 seconds window is a good compromise duration for extracting a current heart rate.

Some embodiments are based on the realization that longer strides are more efficient for training using a larger dataset. Therefore, the stride (in frames) used for windowing during training may be longer (e.g., 60 frames) than the stride used for windowing during inference (e.g., 10 frames). The length of the stride in frames may also be varied depending on the vital sign of the person to be estimated.

In some embodiments, a preamble of a specific time duration (e.g., 0.5 seconds) is added to each window. For instance, a number of additional frames (e.g., 14) are added immediately preceding a start of the window, resulting in a longer duration (e.g., 314 frames) multidimensional time series.

In some embodiments, where the input is an NIR video 105, the multidimensional time-series (e.g., 48 dimensions of the time sequence) is fed into the PPG estimator module 109 as channels. The PPG estimator module 109 comprises a sequence of layers associated with the time-series U-net 109*a* and the RNN 109*b* forming the TURNIP architecture. The channels corresponding to the multidimensional time-series signal are combined during a forward pass through the sequence of layers. In the PPG estimator module 109, the time-series U-Net 109*a* with RNN 109*b* maps the multidimensional time series signal to the desired PPG signal. For each windowed sequence of the multidimensional time-series signal (e.g., the 10-second window), the TURNIP architecture extracts convolutional features at a specific temporal resolution (e.g., three temporal resolutions). The specific temporal resolution may be predefined.

Further, in some embodiments the TURNIP architecture downsamples the inputted time series by a first factor and later by a second factor, where the second factor is an additional factor. The first factor and the second factor for down sampling the input time series may be predefined (e.g., the first factor may be 3 and the second factor may be 2). The PPG estimator module 109 then estimates the desired PPG signal in a deterministic way.

Turnip Architecture:

The TURNIP architecture is a neural network (for example, a DNN) based architecture, which is trained on at least one data set to accurately determine PPG signal(s) based on the multidimensional time-series data. The time-series U-Net 109*a* comprises the contractive path formed by a sequence of contractive layers followed by the expansive path formed by a sequence of expansive layers. The sequence of contractive layers is a combination of convolutional layers, max pooling layers, and dropout layers. Similarly, the sequence of expansive layers is a combination of convolutional layers, upsampling layers, and drop out layers. At least some of the contractive layers downsample their input multidimensional time-series signal and at least some of the expansive layers upsample their input forming pairs of contractive and expansive layers of corresponding resolutions. Further, at least some of the contractive layers and expansive layers are connected through pass-through layers. The plurality of contractive layers forms an encoding sub-network that can be thought of as encoding its input data into a sequence with lower temporal resolution. On the other hand, the plurality of expansive layers forms a decoding sub-network that can be thought of as decoding the input data encoded by the encoding network. Further, at least at some resolutions, the encoding sub-network and the decoding sub-network are connected by a pass-through connection. In parallel with the 1×1 convolutional pass-through connections, a specific recurrent pass-through connection is included. The specific recurrent pass-through connection is implemented using the RNN 109*b*. The RNN 109*b* processes its input sequentially, and the RNN 109*b* is included in each of the pass-through layers.

In a preferred embodiment, the RNN 109*b* is implemented using a gated recurrent units (GRU) 113 architecture to provide temporally recurrent features. In other embodiments, the RNN 109*b* may be implemented using a different RNN architecture, such as a long short-term memory (LSTM) architecture. Some embodiments are based on the realization that GRU is an advancement of the standard RNN. GRU uses gates to control a flow of information, and unlike LSTM, GRU does not have a separate cell state ($C_t$). GRU only has a hidden state ($H_t$). GRU at each timestamp t takes an input $X_t$ and the hidden state $H_{t-1}$ from the previous timestamp t−1. Later it outputs a new hidden state $H_t$ which is then passed to the GRU at the next timestamp. There are primarily two gates in a GRU. The first gate is a reset gate and the other one is an update gate. Some embodiments are based on further realization that GRU is faster to train due to its simpler architecture, compared to other types of RNNs such as a Long Short-Term Memory (LSTM) networks.

Contractive Path:

In the time series U-net 109*a*, the contractive path is formed by the sequence of contractive layers, where each contractive layer comprises a combination of one or more of a convolutional layer, a single downsampling convolutional layer, and a dropout layer. A dropout layer is a regularization layer used to reduce overfitting of a layer (for example, a convolutional layer) that it is used with and improve generalization of the corresponding layer. A dropout layer drops outputs of the layer it is used with (for example, the convolutional layer) with a specific probability p, which is also referred to as a dropout rate. The dropout rate may be predefined or calculated in real time based on a training dataset used for training the TURNIP architecture. In an example embodiment, the dropout rate (or p) of every dropout layer is equal to 0.3.

Alternatively, in some other embodiments, the contractive path of the time series U-net 109*a* may not include the dropout layer. In such embodiments, the contractive path is formed by the sequence of contractive layers, where each contractive layer comprises a combination of one or more of only a convolutional layer and a single downsampling convolutional layer.

Further, in some embodiments of the TURNIP architecture, the sequence of contractive layers is formed by 5 contractive layers. In other embodiments, there may be more than 5 contractive layers, and in still other embodiments, there may be fewer than 5 contractive layers. In the 5 contractive layers, a first contractive layer 116*a* comprises two convolutional layers. The first contractive layer 116*a* processes its input, where the input is a multidimensional time series signal provided as multiple channels, and a multi-channel output generated by the first contractive layer 116*a* is submitted to one of the layers (e.g., the fourth expansive layer 118*d*) in the expansive path. Note that although we refer to all of the layers in the contractive path as "contractive layers" and all of the layers in the expansive path as "expansive layers," in some embodiments not every contractive layer actually contracts the length of its input sequence. For example, in one embodiment illustrated in FIG. 1B, the sequence that is output from the first contractive layer 116*a* has substantially the same length as the sequence that is input to the first contractive layer 116*a*. This is because for the convolutions performed in the first contractive layer, the stride=1. Similarly, not every "expansive layer" actually expands the length of its input sequence. For example, the input to and output of the fourth expansive layer have substantially the same length.

Further, each of a second contractive layer 116*b*, a third contractive layer 116*c*, and a fourth contractive layer 116*d* comprises a convolutional layer (sometimes referred to as a "single downsampling layer," although note as above that not every downsampling layer actually downsamples the length of its input) followed by a dropout layer with a specific dropout rate (e.g., p=0.3). In one embodiment, illustrated in FIG. 1B, the second contractive layer 116*b* (whose convolution has stride=3) and the fourth contractive layer 116*d* (whose convolution has stride=2) each downsamples its input by a factor equal to its stride, while the third 116*c* and fifth 116*e* contractive layers do not downsample their inputs. In this embodiment, downsampling is achieved by the stride of each downsampling layer's convolution, but in alternate embodiments, downsampling could be achieved using other means, such as max pooling or average pooling. The second contractive layer 116*b* receives input channels corresponding to the multidimensional time series signal extracted by the time-series extraction module 101 and submits its output to the third contractive layer 116*c* and the corresponding pass-through layer 113*a*. Further, each of the third and fourth contractive layers receives corresponding input from a previous contractive layer and submits corresponding output to both a corresponding next contractive layer and the corresponding pass-through layer.

The fifth and the last contractive layer in the sequence of five contractive layers comprises two convolutional layers followed by a dropout layer with a specific dropout rate. The fifth contractive layer receives input from the fourth contractive layer and submits its output to one of the expansive layers (e.g., the first expansive layer 118*a*) in the expansive path.

Expansive Path:

In some embodiments, the expansive path comprises a sequence of 5 expansive layers. In one such embodiment, illustrated in FIG. 1B, in the sequence of 5 expansive layers, the first expansive layer 118*a* is configured to perform upsampling, concatenation with the output of its corresponding pass-through layer 113*c*, and convolution on its input time series. Similarly, the third expansive layer 118*c* performs upsampling, concatenation with the output of its corresponding pass-through layer 113*a*, and convolution on its input time series. Each of the second 118*b* and fourth 118*d* expansive layers is configured to perform concatenation with the output of its corresponding pass-through layer and convolution on its input time series. The fourth expansive layer additionally includes a dropout layer with a specific dropout rate (e.g., p=0.3). The fifth expansive layer 118*e* consists of a convolutional layer followed by a dropout layer with a specific dropout rate. To upsample the input data at the first 118*a* and third 118*c* expansive layers, each of these two expansive layers uses an up-converter operation to produce upsampled data at its corresponding input. Further, the upsampled data is used for concatenation and temporal convolution is each of these expansive layers.

Still referring to FIG. 1B, the output of the time-series extraction module 101, which is the multidimensional time series, is provided as channels to the PPG estimator module 109. Therefore, each contractive layer processes a number (Chan_in) of input channels into a number (chan_out) of output channels for a kernel of a specific size (e.g., a kernel of size k=3) and specific stride (e.g., the stride s=1). In some example embodiments, the first contractive layer 116*a* may have Chan_in =48 input channels and Chan_out=64 output channels. Output of the first contractive layer 116*a* is submitted to the fourth expansive layer 118*d*.

Similarly, for the second contractive layer 116*b*, third contractive layer 116*c*, fourth contractive layer 116*d*, and fifth contractive layer 116*e*, input channels ("Chan_in"), output channels ("Chan_out"), a kernel ("kernel_size"), and stride ("stride") are specified, respectively.

In one embodiment illustrated in FIG. 1B, for example, the convolution performed by the second contractive layer 116*b* has 48 input channels and 64 output channels, with a kernel size k=9 and stride s=3. The output of the second contractive layer 116*b* is fed to the third contractive layer 116*c* and to a first pass-through layer 113*a*.

Each pass-through layer, such as the first pass through layer 113*a*, consists of a layer of 1×1 convolutions 117 and an RNN such as a GRU 113, whose respective outputs are concatenated 115 and then passed to a corresponding layer of the expansive path.

The third contractive layer 116*c* has 64 input channels and 128 output channels, and a convolutional kernel of size k=7 with stride s=1. An output of the third contractive layer 116*c* is provided to the fourth contractive layer 116*d* of the contractive path and to a second pass-through layer 113*b*, whose output is passed to the corresponding layer 118*b* of the expansive path. The fourth contractive layer 116*d* has 128 input channels and 256 output channels and a convolution using kernel size 7 and stride 1; an output of the fourth contractive layer 116*d* is provided to the fifth contractive layer 116*e* of the contractive path and to a third pass-through layer 113*c*, which passes its output to the corresponding expansive layer 118*b*. At the final stage of the contractive path, the fifth contractive layer 116*e* has 256 input channels and 512 output channels, a convolutional kernel size of 7, and a stride of 1. Further, the output of the fifth contractive layer 116*e* is provided to the first expansive layer 118*a* of the expansive path.

The first expansive layer 118*a* obtains two inputs, where a first input is obtained from the fifth contractive layer 116*e*, and a second input is obtained from an output of the third pass-through layer 113*c*. The first expansive layer 118*a* processes its inputs and passes on its output to the second expansive layer 118*b*. The second expansive layer 118*b* also obtains two inputs, where a first input corresponds to the output of the first expansive layer 118*a*, and a second input corresponds to the output of the second pass-through layer 113*b*.

Similarly, a first input of the third expansive layer 118*c* corresponds to the output of the second expansive layer 118*b*, and a second input of the third expansive layer 118*c* corresponds to the output of the first pass-through layer 113*a*. Further, the output of the third expansive layer 118*c* is provided to the fourth expansive layer 118*d*.

The fourth expansive layer 118*d* obtains a first input from the third expansive layer 118*c* and a second input from the first contractive layer 116*a*. Output of the fourth expansive layer is provided to the fifth expansive layer, which performs channel reduction (e.g., from 64 channels to 1 channel), followed by a dropout layer.

In some embodiments, the output of the fifth expansive layer 118*e* is the final output of the PPG estimator module 109. This output (e.g., a one-dimensional time series that estimates a PPG waveform) is used to obtain the output 111 of the iPPG system 100.

At each time scale, the convolutional layers of the time series U-net 109*a* process all samples from the time series window (e.g., the 10-second window) in parallel. (The computation that obtains each output time step of each convolution may be performed in parallel with the corresponding computations of the other output time steps of the convolution.) In contrast, the proposed RNN layers (e.g., the GRU layers 113) process the temporal samples sequentially. This temporal recurrence has the effect of extending the temporal receptive field at each layer of the expansive path of the time series U-net 109*a*.

For instance, in an embodiment illustrated in FIG. 1B, after the GRU 113 has run through all time steps in the 10-second window, the resulting sequence of hidden states is concatenated 115 with the output of a more standard pass-through layer (1×1 convolution) 117. The hidden state of the GRU 113 is reinitialized for each 10-second window that is fed to the GRU 113.

More details regarding steps executed by the iPPG system 100 to determine the PPG signal are described below with reference to FIG. 1C.

FIG. 1C illustrates steps of a method 119 executed by the iPPG system 100, according to an example embodiment. At step 119*a*, an NIR monochromatic video (for example, the NIR video 105) of a person is received. The NIR video 105 may comprise a face of a person or any other body part of the person with its skin exposed to a camera recording a video. The iPPG system 100 may include an NIR light source configured to illuminate the skin of the person, for recording the NIR video 105. Further, the iPPG system 100 may be configured to measure intensities indicative of variation of coloration of the skin at different instants of time, where each instant of time corresponds to a video frame, i.e., an image in a sequence of images).

To that end, an image corresponding to each frame of the inputted NIR video is segmented into different regions, where the different regions correspond to different parts of the skin of the person in the image. The different regions of the skin of the person may be identified using landmark detection. For instance, if the body part of the person is the person's face, then the different regions of the face may be obtained using facial landmark detection.

At step 119*b*, the sequence of images that include different regions of the skin of the person is received by the time-series extraction module 101 of the iPPG system 100.

At step 119*c*, the sequence of images is transformed into a multidimensional time-series signal by the time-series extraction module 101. To that end, pixel intensities of the pixels from each spatial region of the plurality of spatial regions 103 (also referred to as "different spatial regions") at an instant of time (e.g., in one video frame image 107) are averaged to produce a value for each dimension of the multidimensional time-series signal for the instant of time.

At step 119*d*, the multidimensional time-series signal is processed by the time-series U-net 109*a* coupled with the recurrent neural network 109*b* in the pass-through layers that form the TURNIP architecture. The multidimensional time-series signal is processed by the different layers of the TURNIP architecture to generate a PPG waveform, which in some embodiments is represented as a one-dimensional (1D) time series.

At step 119*e*, the vital signs, such as heartbeat or pulse rate of the person, are estimated based on the PPG waveform. In some embodiments, the output 111 of the iPPG system 100 comprises the vital signs.

In this way, the PPG estimator module 109 estimates the PPG signal from the multidimensional time-series signal extracted from the NIR video 105. To that end, the multidimensional time-series signal is temporally convolved at each layer of the TURNIP architecture. More details regarding temporal convolution are provided below with respect to FIG. 2A-FIG. 2C. Further, in some embodiments the estimated vital sign signals are rendered on an output device such as a display device. In some embodiments, the estimated vital signals may be further utilized to control operations of one or more external devices associated with the person for whom the vital signals are estimated.

Time Series Extraction from Multi-Channel Video:

In some embodiments, such as those illustrated in FIG. 1A and FIG. 1C, the iPPG system 100 or method 119 starts with single-channel video, such as single-channel NIR video 105, as input. While these figures and corresponding descriptions above apply to single-channel NIR video, it is to be understood that the same ideas can be similarly applied to other single-channel video, such as video collected using a monochromatic grayscale camera sensor, or a thermal infra-red camera sensor.

In other embodiments, however, the iPPG system or method starts with multi-channel video. The discussion of multi-channel images in this document primarily discuss RGB video (i.e., video with red, green, and blue color channels) as an example of multi-channel video. However, it is to be understood that the same ideas can be similarly applied to other multi-channel video inputs, such as multi-channel NIR video, RGB-NIR four-channel video, multi-spectral video, and color video that is stored using a different color-space representation than RGB, such as YUV video, or a different permutation of the RGB color channels such as BGR.

With multi-channel video, such as RGB video, there are multiple methods for the time series extraction module to extract a time series from the multi-channel video, and different embodiments use different methods for time series extraction from multi-channel video. FIGS. 1E-1H illustrate some of these methods, which are each used in different embodiments of the invention.

Figure 1E:
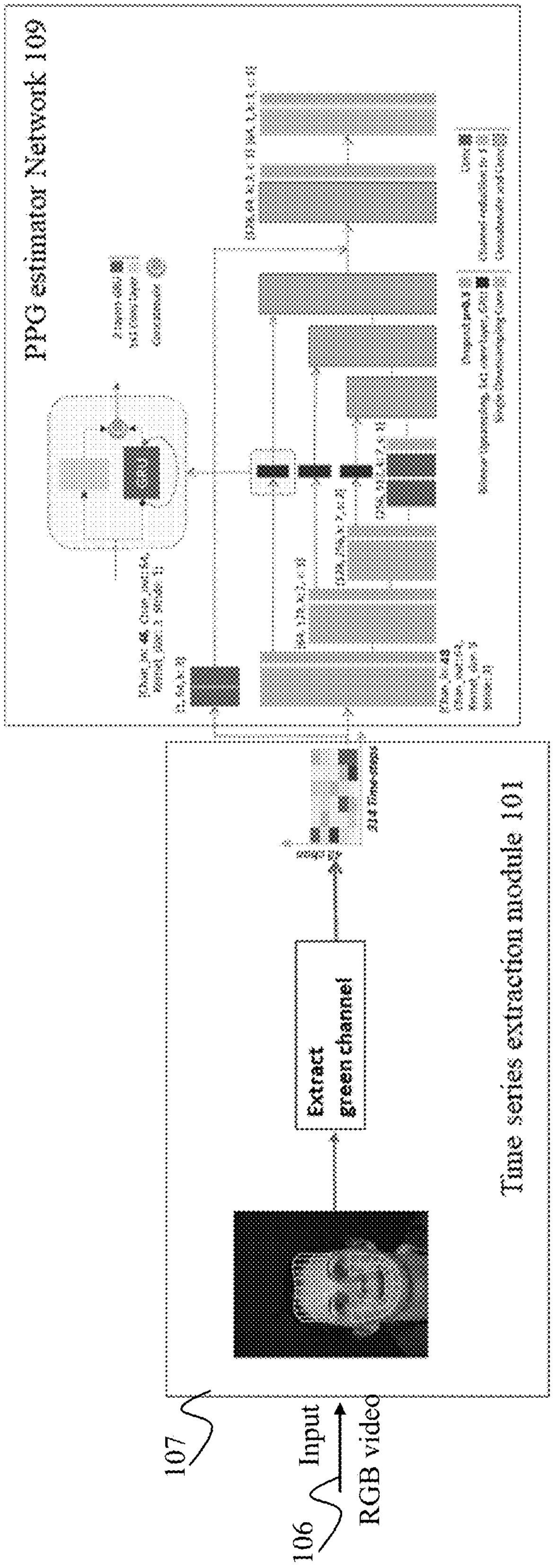
FIG. 1E illustrates a functional diagram of iPPG system that extracts information from a single color channel of the video, according to an example embodiment

FIG. 1E shows an example embodiment in which the input is an RGB video 106. In this embodiment, all but one of the color channels is ignored, and the time series extraction module 101 extracts a multidimensional time series from only a single channel, for instance the green (G) channel, using methods similar to those described herein for extracting a multidimensional time series from single-channel video such as NIR video. The green channel is used because of the three color channels red, green, and blue, the green channel intensity has been shown to be the one most affected by the blood volume changes detected by iPPG. As in the monochromatic case the output of the time-series extraction module 101 is fed into the PPG estimator 109. Each dimension of the multidimensional time series is fed into the PPG estimator 109 by treating it as an input channel A disadvantage of this approach is that it ignores all information in the other two color channels. It has been demonstrated, for example, that using three color channels rather than one can help to distinguish intensity changes due to pulsatile blood volume changes (which affect the green channel more than the other two color channels) from intensity changes due to nuisance factors, such as subject motion and global lighting changes (which, e.g., may affect all three color channels more equally).

Figure 1F:
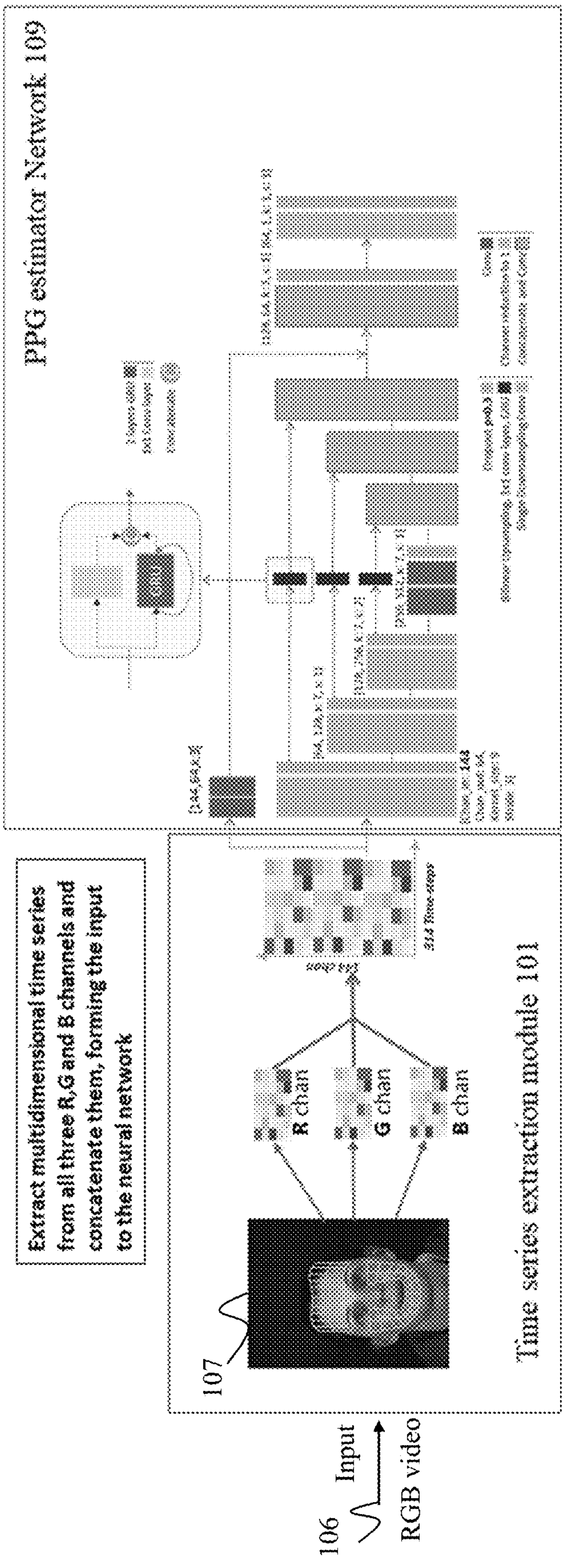
FIG. 1F illustrates a functional diagram of iPPG system that stacks the multidimensional time series for every color channel of every region along a single channel dimension, according to an example embodiment.

FIG. 1F shows an example embodiment where from each of the R, G, and B channels a multi-dimensional time series (e.g., a time series with 48 dimensions corresponding to 48 ROIs) is extracted, using methods similar to those described herein for extracting a multidimensional time series from single-channel video such as NIR video. This results in a multi-dimensional time series (e.g., a 48-channel time series) extracted from each of the red channel ("R chan"), the green channel ("G chan"), and the blue channel ("B chan"). These three multi-channel times series are concatenated along the channel dimension to form a single multidimensional time series (e.g., with 3•48=144 channels), which is fed into the PPG estimator 109. Each dimension of the multidimensional time series is fed into the PPG estimator 109 by treating it as an input channel. One disadvantage of this approach is that the concatenation obfuscates the correspondence between channels obtained by the different channels from a same ROI.

Figure 1G:
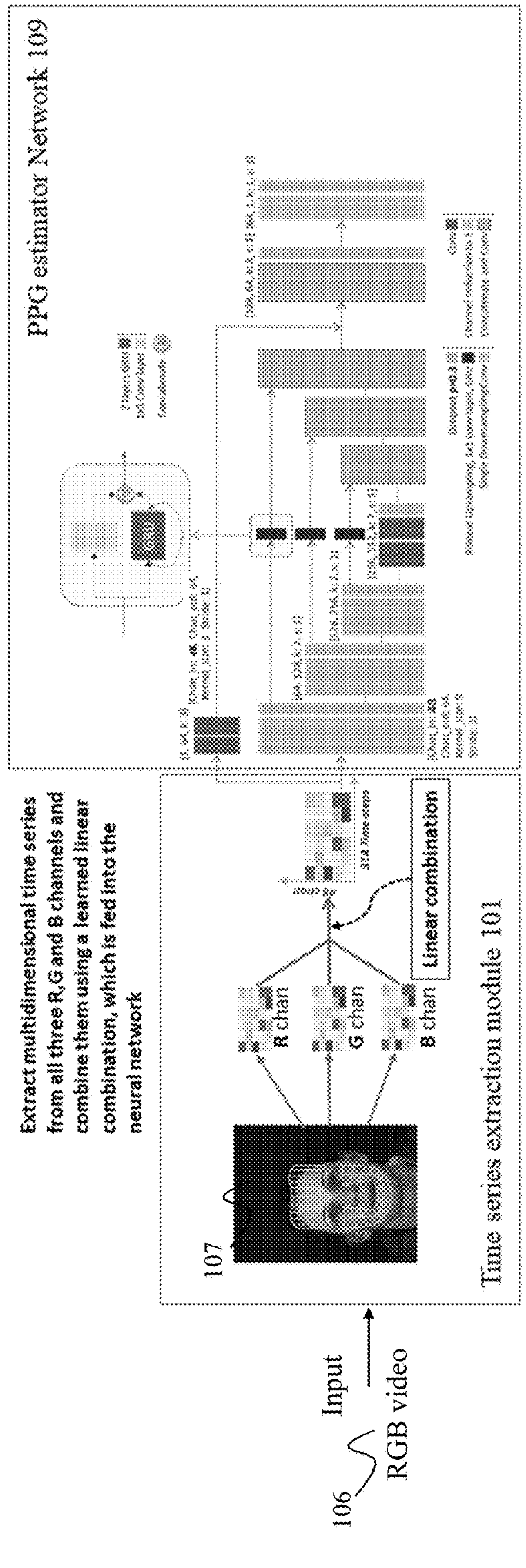
FIG. 1G illustrates a functional diagram of iPPG system in which multidimensional time series for multiple color channels are combined into a single multidimensional time series, according to an example embodiment.

FIG. 1G shows another example embodiment where from each of the R, G, and B channels a multi-dimensional time series (e.g., a time series with 48 dimensions corresponding to 48 ROIs) is extracted, using methods similar to those described herein for extracting a multidimensional time series from single-channel video such as NIR video. This again results in a multi-dimensional time series (e.g., a 48-channel time series) extracted from each of the red channel ("R chan"), the green channel ("G chan"), and the blue channel ("B chan"). In this case, the multidimensional time series from each of the color channels R,G, and B are linearly combined to form a single multidimensional time series, whose dimensions are the same as the dimensions of each channel's multidimensional time series (e.g., 48 channels×314 time steps), which is fed into the PPG estimator 109. In some embodiments, the coefficients used for the linear combination are learned in conjunction with the parameters of the neural network. In other embodiments, the coefficients may be chosen a priori, for example based on standard color-space conversions from RGB to grayscale. Each dimension of the multidimensional time series is fed into the PPG estimator 109 by treating it as an input channel.

One disadvantage of this approach is that it can only learn a single linear combination to combine the three color channels into one. The same linear combination must be used for all regions, and the linear combination is independent of the data (e.g., the same linear combination must be used by all subjects, of all skin tones, in all lighting conditions).

Figure 1H:
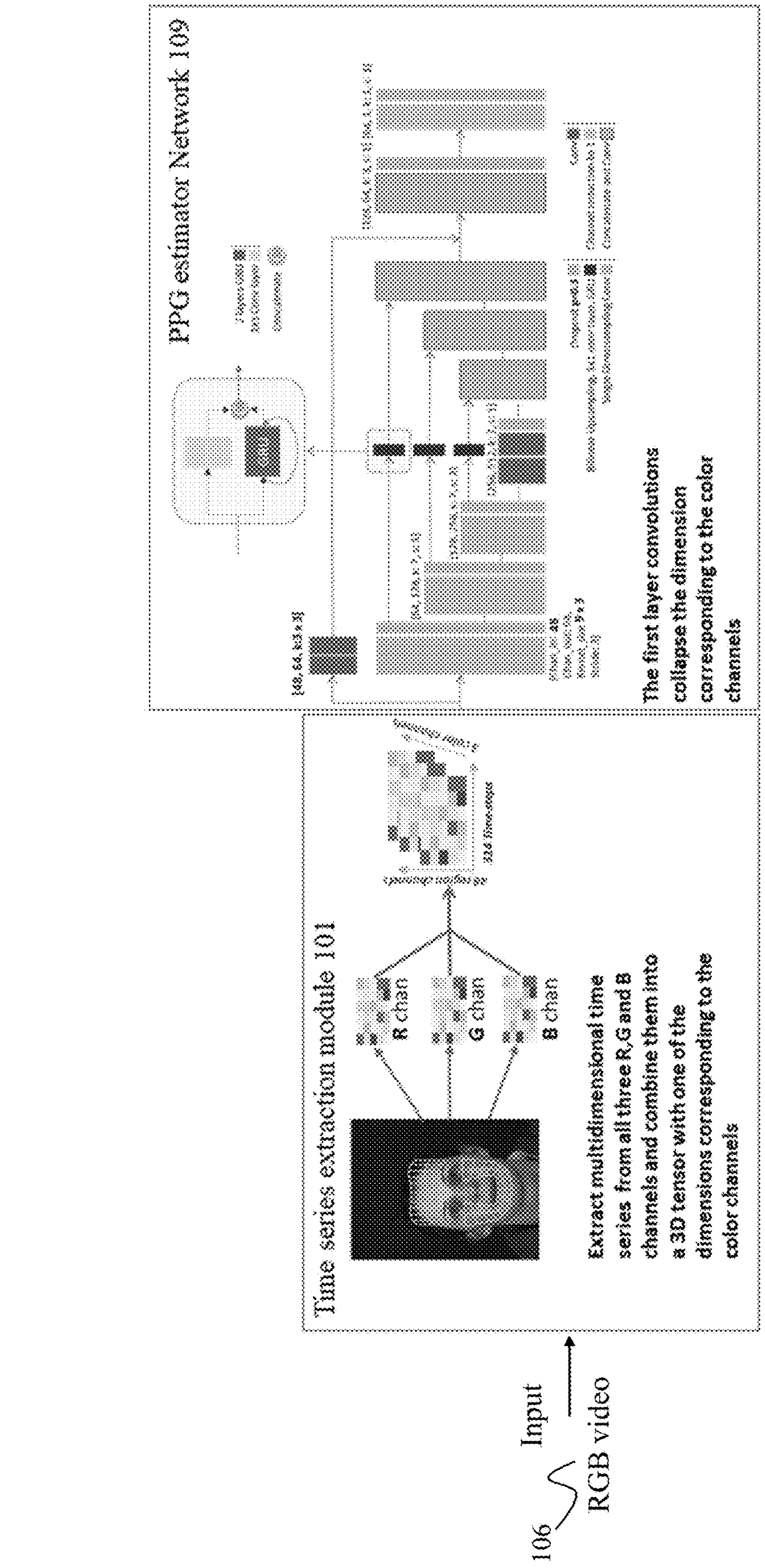
FIG. 1H illustrates a functional diagram of iPPG system that stacks the multidimensional time series for every color channel of every region along two different channel dimensions, according to an example embodiment.
Figure 11:
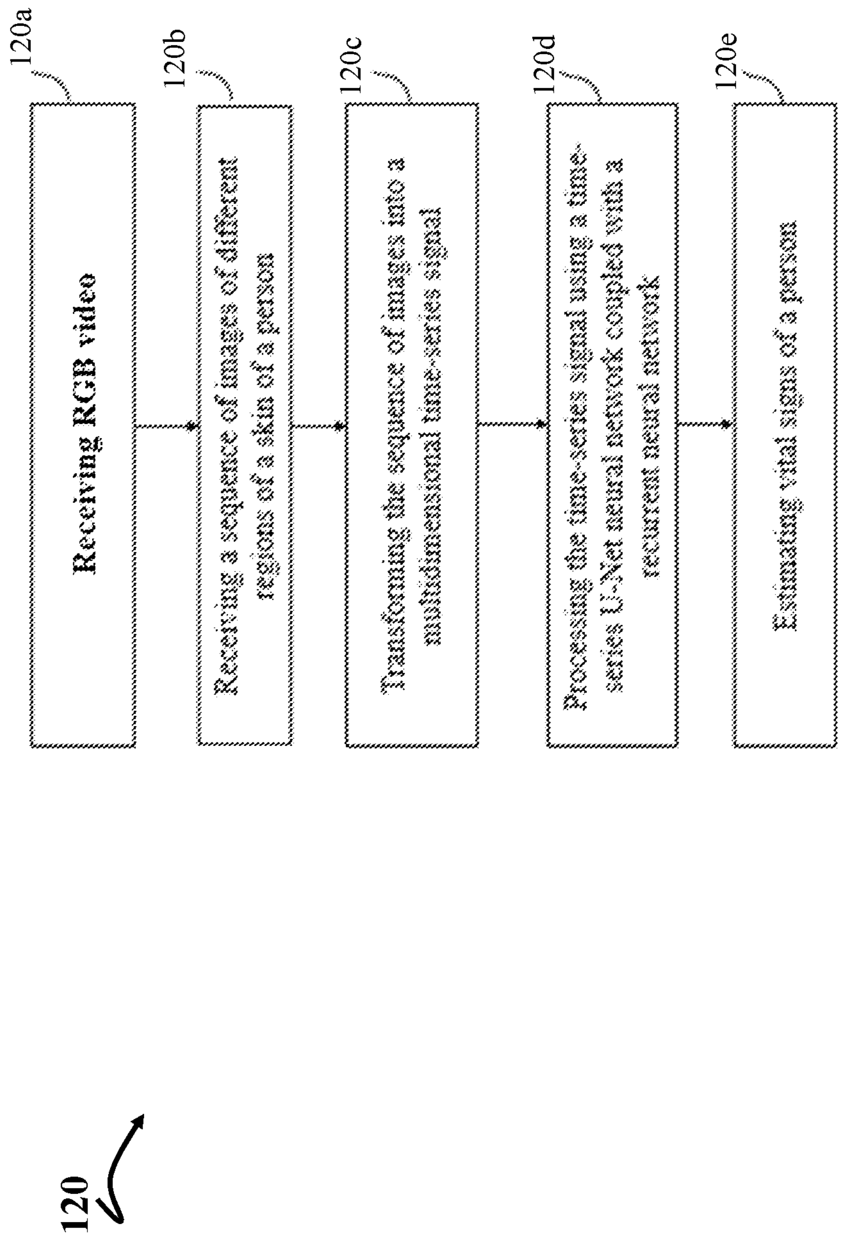

FIG. 1H shows an alternative embodiment where from each of the R, G, and B channels a multi-dimensional time series (e.g., a time series with 48 dimensions corresponding to 48 ROIs) is extracted, using methods similar to those described herein for extracting a multidimensional time series from single-channel video such as NIR video. This again results in a multi-dimensional time series (e.g., a 48-channel time series) extracted from each of the red channel ("R chan"), the green channel ("G chan"), and the blue channel ("B chan"). In this case, multidimensional time series from each of the color channels R,G, and B are shaped into a three-dimensional (3D) array, also known as a 3D tensor. The three dimensions of this array correspond to time (e.g., 314 time steps), facial region (e.g., 48 region channels), and color channel (e.g., 3 color channels). This array forms the input to the PPG estimator 109. The convolution kernels of the first and second contractive layers are constructed so that the color dimension is collapsed to a single dimension at the output of each layer. This approach can overcome the disadvantages of the approaches described in FIG. 1E-FIG. 1H.

FIG. 1I illustrates the steps of a method 120 executed by the iPPG system 100, according to an example embodiment in which multi-channel video, e.g., RGB video, is received 120*a*. At step 120*a*, an RGB video (for example, the RGB video 106) of a person is received. The RGB video 106 may comprise a face of a person or any other body part of the person with its skin exposed to a camera recording a video. Further, the iPPG system 100 may be configured to measure intensities indicative of variation of coloration of the skin at different instants of time, where each instant of time corresponds to a video frame, i.e., an image in a sequence of images).

To that end, an image corresponding to each frame of the inputted NIR video is segmented into different regions, where the different regions correspond to different parts of the skin of the person in the image. The different regions of the skin of the person may be identified using landmark detection. For instance, if the body part of the person is the person's face, then the different regions of the face may be obtained using facial landmark detection.

At step 120*b*, the sequence of images that include different regions of the skin of the person is received by the time-series extraction module 101 of the iPPG system 100.

At step 120*c*, the sequence of images is transformed into a multidimensional time-series signal by the time-series extraction module 101. To that end, pixel intensities in each color channel of the pixels from each spatial region of the plurality of spatial regions 103 (also referred to as "different spatial regions") at an instant of time (e.g., in one video frame image 107) are averaged to produce a value for each dimension of a multidimensional time-series signal for the color channel for the instant of time. From the color-channel multidimensional time series, a single multidimensional time series is extracted, e.g., using one of the methods described in FIG. 1E-FIG. 1H.

At step 120*d*, the multidimensional time-series signal is processed by the time-series U-net 109*a* coupled with the recurrent neural network 109*b* in the pass-through layers that form the TURNIP architecture. The multidimensional time-series signal is processed by the different layers of the TURNIP architecture to generate a PPG waveform, which in some embodiments is represented as a one-dimensional (1D) time series.

At step 120*e*, the vital signs, such as heartbeat or pulse rate of the person, are estimated based on the PPG waveform. In some embodiments, the output 111 of the iPPG system 100 comprises the vital signs.

In this way, the PPG estimator module 109 estimates the PPG signal from the multidimensional time-series signal extracted from the RGB video 106. To that end, the multidimensional time-series signal is temporally convolved at each layer of the TURNIP architecture. More details regarding temporal convolution are provided below with respect to FIG. 2A-FIG. 2C. Further, in some embodiments the estimated vital sign signals are rendered on an output device such as a display device. In some embodiments, the estimated vital signals may be further utilized to control operations of one or more external devices associated with the person for whom the vital signals are estimated.

Figure 2A:
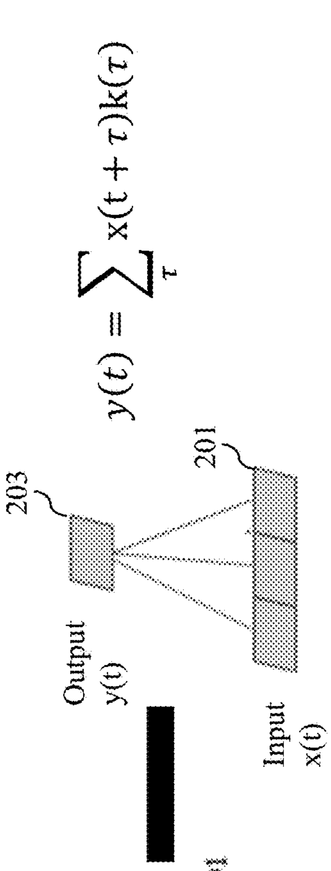
FIG. 2A illustrates a temporal convolution of an input channel operated by a kernel of size 3 with stride 1, according to an example embodiment.
Figure 2A:
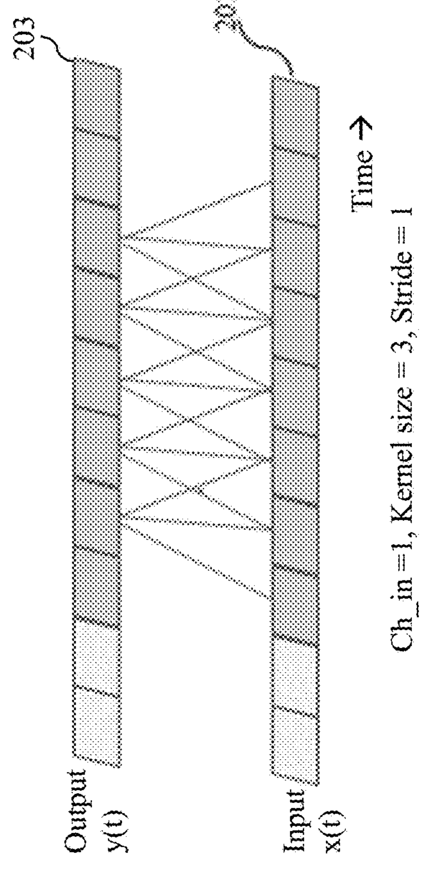
Figure 2B:
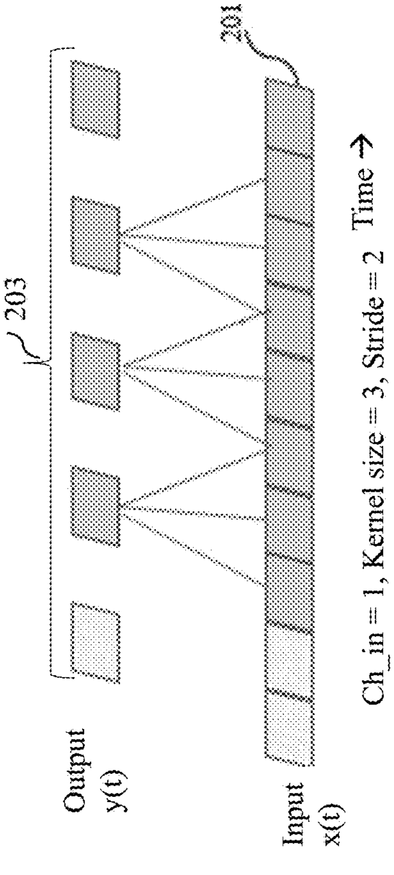
FIG. 2B illustrates the temporal convolution of the input channel operated by a kernel of size 3 with stride 2, according to an example embodiment.
Figure 2C:
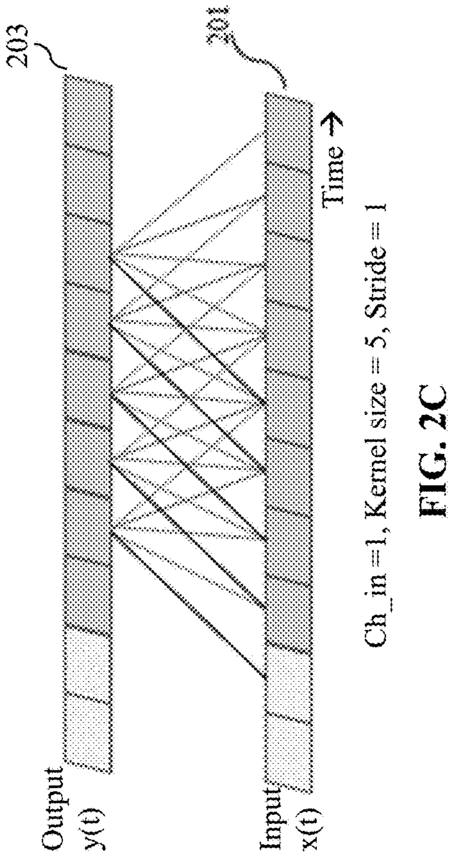
FIG. 2C illustrates the temporal convolution of the input channel operated by a kernel of size 5 with stride 1, according to an example embodiment.

FIG. 2A illustrates a temporal convolution of an input channel 201 operated on by a kernel of size 3 with stride 1, according to an example embodiment. FIG. 2B illustrates the temporal convolution of the input channel 201 operated on by a kernel of size 3 with stride 2, according to an example embodiment. FIG. 2C illustrates the temporal convolution of the input channel 201 operated on by a kernel of size 5 with stride 1, according to an example embodiment.

In FIG. 2A, assume that the times series 201 in the single input channel (Ch_in=1) is obtained by one of the convolutional layers (for example, a convolutional layer in the first contractive layer) of the time-series U-net 109*a*, where a length of the input channel 201 is 10. The input channel 201 corresponds to one dimension of a multidimensional time series fed to the PPG estimator module 109 by the time-series extraction module 101 (e.g., the input channel 201 is a one-dimensional time series sequence). Further, based on the stride value used to operate on the input channel, the length of the corresponding output 203 channel is varied.

Let each block drawn in the figure of the input channel x(t) 201 represent the value of the channel at one time step. Further, let each coefficient of the kernel be denoted by k(τ). Assume that a size of the kernel used for convolution with the input channel 201 by the convolutional layer is 3. Since the kernel size is 3, the kernel comprises 3 coefficients, corresponding to τ=−1, 0, and 1. Further, assume that the kernel is traversed (or shifted) over the input channel 201 with a stride value of s=1 (the stride value can also be referend to as "stride length"). Further, the output of the convolution is obtained in output channel y(t) 203. Accordingly, temporal convolution is calculated as:

$$y(t)=\Sigma_{\tau}x(t+\tau)k(\tau), \qquad (1)$$

where τ=−1, 0, and 1. Thus, kernel coefficients (also referred to as "Learnable filter") are k(−1), k(0), k(1).

Similarly, in FIG. 2B and FIG. 2C, the temporal convolution is calculated using the equation (1). In FIG. 2B, the kernel size is 3 which is the same as the kernel size used in FIG. 2A. However, length of the stride is increased to 2. Accordingly, length of the output time series (in channel y(t)) is reduced. In this way, the convolution in FIG. 2B downsamples the input by a factor of 2.

Figure 3:
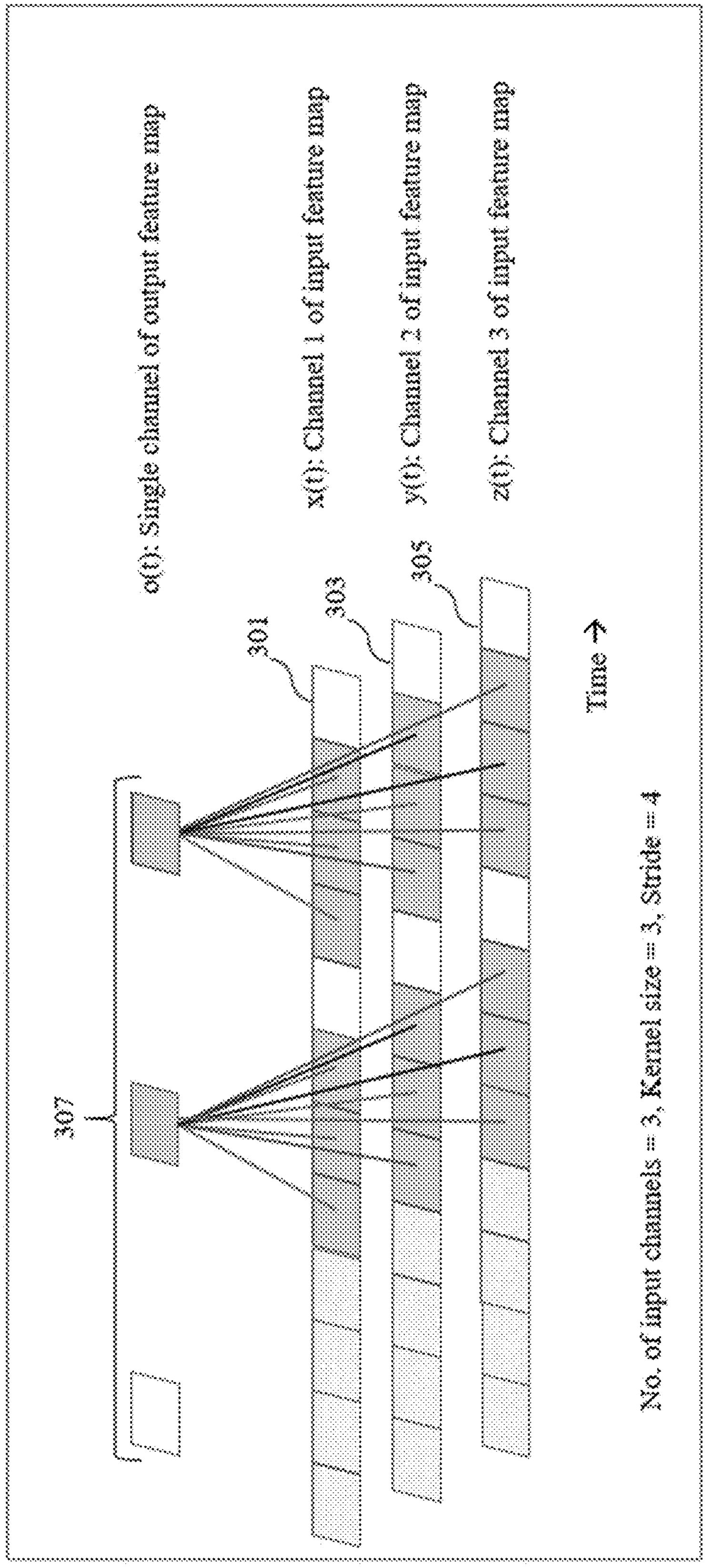
FIG. 3 illustrates temporal convolution with multi-channel input, according to an example embodiment.

FIG. 3 illustrates temporal convolution with multi-channel input, according to an example embodiment. The temporal convolution with multi-channel input is based on the temporal convolution with single channel input as illustrated in FIG. 2A-2C. The PPG estimator module 109 uses the temporal convolution with multi-channel input, where multi-channel input corresponds to a multidimensional time-series signal output by the time-series extraction module 101, or output by a previous layer of the PPG estimator network 109.

In FIG. 3, three input channels are considered for the ease of explanation. However, the number of input channels for a convolution in the PPG estimator module 109 the dimensions of multidimensional time-series input to the convolutional layer. For example, if the multidimensional time-series signal has 48 dimensions corresponding to 48 facial ROIs, then the number of channels input to the convolutions in the first two contractive layers is also equal to 48.

Thus, the three input channels are a channel 1 of an input feature map (also referred to as "a first channel") 301, a channel 2 of an input feature map (also referred to as "a second channel") 303, and a channel 3 of an input feature map (also referred to as "a third channel") 305. Let the first channel 301 be denoted as x(t), the second channel 303 be denoted as y(t), and the third channel 305 be denoted as z(t), and an output channel 307 generated after the temporal convolution of the multiple channels (301-305) be denoted as o(t). Further, let the kernel size be 3, which is shifted on each of the three input channels (301-305) with a stride value of 4 frames. The temporal convolution for the multiple input channels (301-305) is calculated based on the equation (1) for each input channel. The temporal convolution is performed with as many filters as there are channels of the output feature map. In some embodiments, a learnable bias is also added to the output of each filter. In some embodiments, at least one of the temporal convolutions is followed by a non-linear activation function, such as a rectified linear unit (RELU) or sigmoidal activation function.

Further, the outputs of temporal convolutions are passed to the RNN 109*b* via the pass-through layers (FIG. 1B), where inputs to the RNN 109*b* are processed sequentially.

Figure 4:
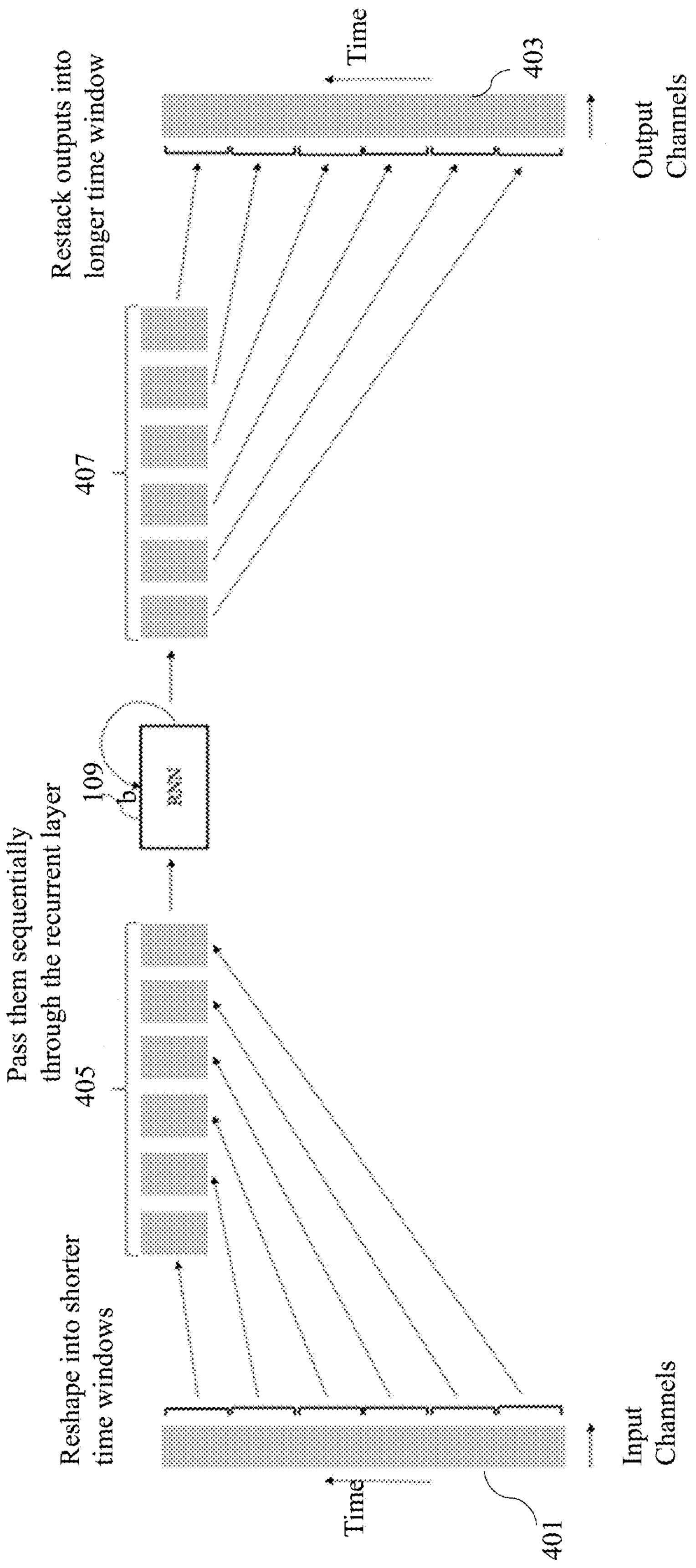
FIG. 4 illustrates sequential processing performed by a recurring neural network (RNN), according to an example embodiment.

FIG. 4 illustrates sequential processing performed by the RNN 109*b* (e.g., by the GRU 113 in FIG. 1B), according to an example embodiment. The RNN 109*b* is configured to sequentially process data from an input multidimensional time series 401, whose dimensions (time×input channels) respectively represent the number of time steps in the input time series and the number of channels in the input time series. To that end, the input time series 401 is reshaped into a plurality of shorter time windows 405, each with the same number of channels as the input time series 401. The windows 405 are then passed sequentially to the RNN 109*b*. In a preferred embodiment, the RNN 109*b* is implemented as a GRU (such as the GRU 113). Alternatively, in some embodiments, the RNN 109*b* may be implemented using a long short-term memory (LSTM) neural network.

After the RNN has sequentially processed all of the shorter time windows 405 of the input time series 401, The sequential outputs 407 of the RNN 109*b* are restacked into a longer time window to form the output time series 403 of the RNN, whose dimensions (time×input channels) respectively represent the number of time steps in the output time series (which in some embodiments is the same as the number of time steps in the input time series) and the number of channels in the output time series. In some embodiments, the restacking of the outputs 407 into the output time series may be in the reverse order to the stacking illustrated in FIG. 4.

Once the entire input time series 401 has been passed sequentially through the RNN and restacked into the output time series 403, it is ready to be concatenated (e.g., concatenation 115 in FIG. 1B) with the time series output obtained by processing the same input time series using a more standard U-net pass-through (e.g., the 1×1 convolution 117 in FIG. 1B) that was performed using a parallel (i.e., not inherently sequential) computation.

At each time scale, the convolutional layers of the time series U-net 109*a* process all samples from the time series window (e.g., the 10-second window) in parallel. (The computation that obtains each output time step of each convolution may be performed in parallel with the corresponding computations of the other output time steps of the convolution.) In contrast, the proposed RNN layers (e.g., the GRU layers 113) process the temporal samples sequentially. This temporal recurrence has the effect of extending the temporal receptive field at each layer of the expansive path of the time series U-net 109*a*.

In this way, the sequential temporal processing of the RNN 109*b* is coupled with the temporally parallel processing of a time-series U-Net 109*a*, enabling the PPG estimator module 109 to more accurately estimate the PPG signal from the multidimensional time-series signals.

Some embodiments are based on recognition that in a narrow frequency band including a near-infrared frequency of 940 nm, the signal observed by the NIR camera is significantly weaker than a signal observed by a color intensity camera, such as an RGB camera. However, the iPPG system 100 is configured to handle such weak intensity signals by using a bandpass filter. The bandpass filter is configured to denoise measurements of pixel intensities of each spatial region of the different spatial regions. More details regarding processing of the NIR signal to estimated iPPG signal is described below with reference to FIG. 5.

Figure 5:
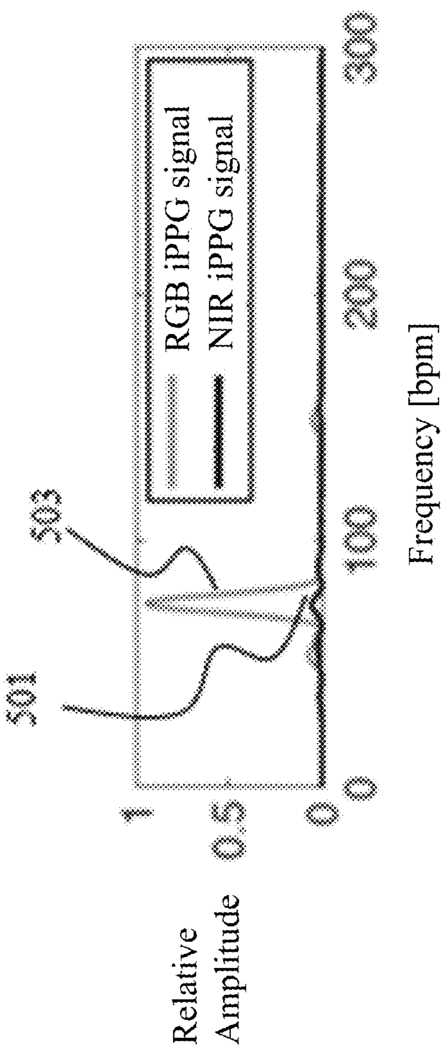
FIG. 5 shows a plot for comparison of PPG signal frequency spectra obtained using near-infrared (NIR) and the visible portion of the spectrum (RGB), according to an example embodiment.

FIG. 5 shows a plot for comparison of PPG signal frequency spectra obtained using NIR and the visible portion of the spectrum (RGB), according to an example embodiment. As can be seen from FIG. 5, the iPPG signal 501 in NIR (labeled "NIR iPPG signal" in the legend) is roughly 10 times weaker than that in RGB 503 (labeled "RGB iPPG signal"). Therefore, in some embodiments, the iPPG system 100 includes a near-infrared (NIR) light source to illuminate the skin of the person, wherein the NIR light source provides illumination in a first frequency band, as well as a camera including a processor to measure the intensities of each of the different regions in a second frequency band overlapping the first frequency band, such that the measured intensities of a region of the skin are computed from intensities of pixels of an image of the region of the skin.

In some embodiments, the first frequency band and the second frequency band include a near-infrared frequency of 940 nm. The iPPG system 100 may include a filter to denoise the measurements of the intensities of each of the different regions. To that end, techniques such as robust principal components analysis (RPCA) may be used. In an embodiment, the second frequency band has a passband of width less than 20 nm, e.g., the bandpass filter has a narrow passband whose full width at half maximum (FWHM) is less than 20 nm. In other words, the overlap between the first frequency band and the second frequency band is less than 20 nm wide.

Some embodiments are based on the realization that optical filters such as bandpass filters and long-pass filters (i.e., filters that block transmission of light having a wavelength less than a cutoff frequency but allow transmission of light having a wavelength greater than a second cutoff frequency) may be highly sensitive to an angle of incidence of the light passing through the filter. For example, an optical filter may be designed to transmit and block specified frequency ranges when the light enters the optical filter parallel to the axis of symmetry of the optical filter (roughly perpendicular to the optical filter's surface), which may be an angle of incidence of 0°. When an angle of incidence varies from 0°, many optical filters exhibit "blue shift," in which the passband and/or cutoff frequencies of the filter effectively shift to shorter wavelengths. To account for the blue shift phenomenon, some embodiments use a center frequency of the overlap between the first and second frequency bands to have a wavelength greater than 940 nm (e.g., the center frequency of a bandpass optical filter or the cutoff frequencies of a long-pass optical filter are shifted to have a longer wavelength than 940 nm).

As light from different parts of the skin may be incident upon the optical filter at different angles of incidence, the optical filter allows different transmission of the light from different parts of the skin. In response, some embodiments use a bandpass filter with a wider passband (e.g., the bandpass optical filter that has a passband wider than 20 nm), and hence the overlap between the first and second frequency bands is greater than 20 nm wide.

In some embodiments, the iPPG system 100 uses the narrow frequency band including the near-infrared frequency of 940 nm to reduce the noise due to illumination variations. As a result, the iPPG system 100 provides accurate estimation of the vital signs of the person.

Some embodiments are based on the realization that illumination intensity across a body part (e.g., a face of the person) can be non-uniform due to factors such as variation in 3D directions of the normals across the face surface, due to shadows cast on the face, and due to different parts of the face being at different distances from the NIR light source. To make the illumination more uniform across the face, some embodiments use a plurality of NIR light sources (e.g., two NIR light sources placed on each side of the face and at approximately equal distances from the head). In addition, horizontal and vertical diffusers are placed on the NIR light sources to widen the light beams reaching the face, to minimize the illumination intensity difference between the center of the face and the periphery of the face.

Some embodiments aim to capture well-exposed images of the skin regions in order to measure strong iPPG signals. However, the intensity of the illumination is inversely proportional to square of a distance from the light source to the face. If the person is too close to the light source, the images become saturated and may not contain the iPPG signals. If the person is at a farther distance from the light source, the images may become dimmer and have weaker iPPG signals. Some embodiments may select the most favorable position of the light sources and their brightness setting to avoid capturing saturated images, while recording well-exposed images at a range of possible distances between the skin regions of the person and the camera.

The type of U-net architecture used in the time-series U-Net 109*a* in some embodiments, such as the embodiment illustrated in FIG. 1B, is sometimes referred to as a "V-net", because the contractive path of the U-net uses strided convolution instead of a max-pooling operation to reduce the size of the feature maps in the contractive layers. In another embodiment, the time-series U-net 109*a* may be replaced by any other U-Net based architecture, such as a U-net that uses max pooling in the contractive layers. In other example embodiments, the RNN 109*b* may be implemented using at least one of a GRU architecture or a long short-term memory (LSTM) architecture.

Further, to enable the PPG estimator module 109 to accurately estimate the PPG signal, the PPG estimator module 109 is trained. Details regarding the training of the PPG estimator module 109 are described below.

Training of TURNIP (PPG Estimator Module):

For training TURNIP, one or more training loss functions may be used. The one or more training loss functions are used to determine optimal values of weights to weigh features such that similarity between ground truth values and estimated values is maximized. For instance, let y denote a ground truth PPG signal and $\bar{y}(\theta)$ denote the estimated PPG signal in the time domain. In some embodiments, a learning objective for training TURNIP is to find optimal network weights $\theta^*$ that maximize the Pearson correlation coefficient between the ground truth and the estimated PPG signals. Therefore, the training loss function G(x, z) for any two vectors x and z of a length T is defined as:

$$G(x, z) = 1 - \frac{T \cdot x^T z - \mu_x \mu_z}{\sqrt{(T \cdot x^T x - \mu_x^2)(T \cdot z^T z - \mu_z^2)}}, \tag{2}$$

where $\mu_x$ and $\mu_z$ are the sample means of x and z, respectively. The one or more loss functions may include one or both of temporal loss (TL) and spectral loss (SL).

To minimize TL, network (i.e., TURNIP) parameters are found such that:

$$\theta^* = \arg\min_{\theta} G(y, \bar{y}(\theta)), \tag{3}$$

To minimize SL, in some embodiments inputs to the loss function are first transformed to a frequency domain, e.g. using a fast Fourier transform (FFT), and any frequency components lying outside of desired range of frequencies are suppressed. For example, for heart rates, the frequency components lying outside of the range [0.6, 2.5] Hz band are suppressed because they are outside a typical range of human heart rates. In this case, the network parameters are computed to solve:

$$\theta^* = \arg\min_{\theta} G(|Y|^2, |\bar{Y}(\theta)|^2), \tag{4}$$

where Y=FFT(y) and $\bar{Y}$=FFT($\bar{y}$), and |•| denotes the complex modulus operator.

Training Dataset:

In an example embodiment, TURNIP is trained based on MERL-Rice Near-Infrared Pulse (MR-NIRP) Car Dataset. The dataset contains face videos recorded with an NIR camera, fitted with a 940±5 nm bandpass filter. Frames were recorded at 30 frames per second (fps), with 640×640 resolution and fixed exposure. The ground truth PPG waveform is obtained using a finger pulse oximeter (for example, CMS 50D+) recording at 60 fps, which is then down sampled to 30 fps and synchronized with the video recording. The dataset features 18 subjects and is divided into two main scenarios, labeled Driving (city driving) and Garage (parked with engine running). Further, only "minimal head motion" condition is evaluated for each scenario. The dataset includes female and male subjects, with and without facial hair. Videos are recorded both at night and during the day in different weather conditions. All recordings for the garage setting are 2 minutes long (3,600 frames), and during driving range from 2 to 5 minutes (3,600-9,000 frames).

Further, the training dataset consists of subjects with heart rates ranging from 40 to 110 beats per minute (bpm). However, the heart rates of test subjects are not uniformly distributed. For most subjects, the heart rate ranges roughly from 50 to 70 bpm. The dataset has a smaller number of outliers. Therefore, a data augmentation technique is used to address both (i) the relatively small number of subjects and (ii) gaps in the distribution of subject heart rates. At training time, for each 10-second window, in addition to using the 48-dimensional PPG signal that is output by the time series extraction module 101, a signal with linear resampling rates 1+r and 1−r is also resampled, where a value of $r \in [0.2, 0.6]$ is randomly chosen, for each 10-second window.

Therefore, the data augmentation is useful for those subjects with out-of-distribution heart rates. Accordingly, it is desirable to train TURNIP with as many examples as possible for a given frequency range.

In an example embodiment, TURNIP is trained for 10 epochs, and the trained model is used for testing (also called "inference"). In another embodiment, TURNIP may be trained for fewer than 10 epochs. In an example embodiment, the Adam optimizer is selected, with a batch size of 96 and a learning rate of $1.5 \cdot 10^{-4}$. The learning rate is reduced at each epoch by a factor of 0.05. Further, a train-test protocol of leave-one-subject-out cross-validation is used. At test time (i.e., inference time), the test subject's time-series is windowed using the time-series extraction module 101, and the heart rate is estimated sequentially with a stride of 10 samples between the windows. In an example embodiment, one heart rate estimate is outputted for every 10 frames.

Further, the performance of the system is evaluated using two metrics. The first metric, percent of time the error is less than 6 bpm (PTE6), indicates the percentage of heart rate (HR) estimations that deviate in absolute value by less than 6 bpm from the ground truth. The error threshold is set to 6 bpm as that is the expected frequency resolution of a 10-second window. The second metric is root-mean-squared error (RMSE) between the ground-truth and estimated HR. The second metric is measured in bpm for each 10-second window and averaged over the test sequence.

The standard deviation of the iPPG system 100 for PTE6 is considerably higher without data augmentation, indicating a high variability across subjects. Further, impact of data augmentation on tested subjects is analyzed.

Figure 6A:
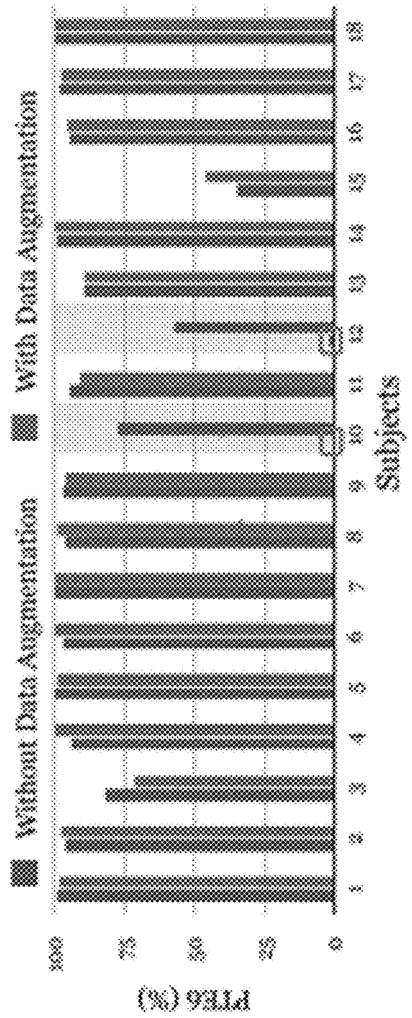
FIG. 6A illustrates impact of data augmentation on heart rate estimation using a PTE6 (percent of time the error is less than 6 bpm) metric, according to an example embodiment.
Figure 6B:
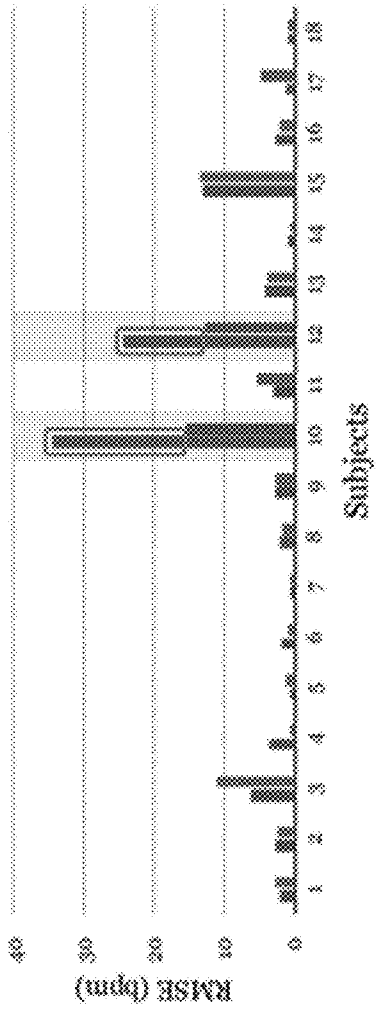
FIG. 6B illustrates impact of data augmentation on heart rate estimation using a root-mean-squared error (RMSE) metric, according to an example embodiment.

FIG. 6A illustrates impact of data augmentation on percent of time the error is less than 6 bpm (PTE6 metric), according to an example embodiment. FIG. 6B illustrates impact of data augmentation on root mean-squared error (RMSE) metric, according to an example embodiment. Portions of FIGS. 6A and 6B covered by rectangles indicate poor performance of the iPPG system 100 without data augmentation for two subjects with out-of-distribution heart rates. Subjects 10 and 12 have the lowest and highest resting heart rates in the dataset, ~40 and ~100 bpm respectively. Thus, when testing on either of those subjects, the training set contains no subjects with similar heart rates. Without data augmentation, the TURNIP fails completely for those subjects. With data augmentation, it is much more accurate.

Further, the impact of the GRU cell in the pass-through connection is analyzed. The GRUs process the feature maps sequentially at multiple time resolutions. Thus, they extract features beyond the local receptive field of convolutional kernels used at the convolutional layers of the TURNIP. The addition of the GRU improves performance of the iPPG system 100. Further, the two training loss functions TL and SL used for training are compared.

Figure 7:
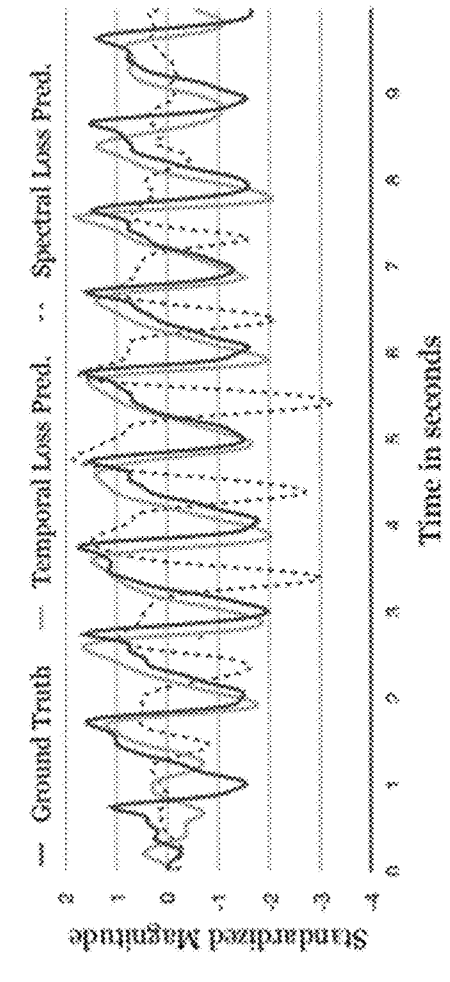
FIG. 7 shows comparison of PPG signal estimated by a Time-series U-net with Recurrence for NIR Imaging PPG (TURNIP) trained using temporal loss (TL) and that estimated by a TURNIP trained using spectral loss (SL) for a test subject, in comparison with a corresponding ground truth PPG signal, according to an example embodiment.

FIG. 7 shows comparison of PPG signal estimated by the TURNIP trained using TL and the TURNIP trained using SL for a test subject, according to an example embodiment. FIG. 7 compares SL vs. TL for the estimated PPG signals for 10 seconds for a test subject. From FIG. 7, it is evident that performance of the TURNIP trained using SL in estimation of the PPG signal is lower compared to that of TL. As shown in the FIG. 7, the TURNIP trained with TL generates a much better estimate of the ground-truth PPG signal. While the recovered signal with SL has a similar frequency, it often does not match the peaks and distorts the signal amplitude or shape. That is, the spectrum of the recovered signal and the heart rate are similar in both cases, but not the temporal variations. Therefore, in a preferred embodiment, TURNIP may be trained using TL training loss function.

Exemplar Embodiments

Figure 8:
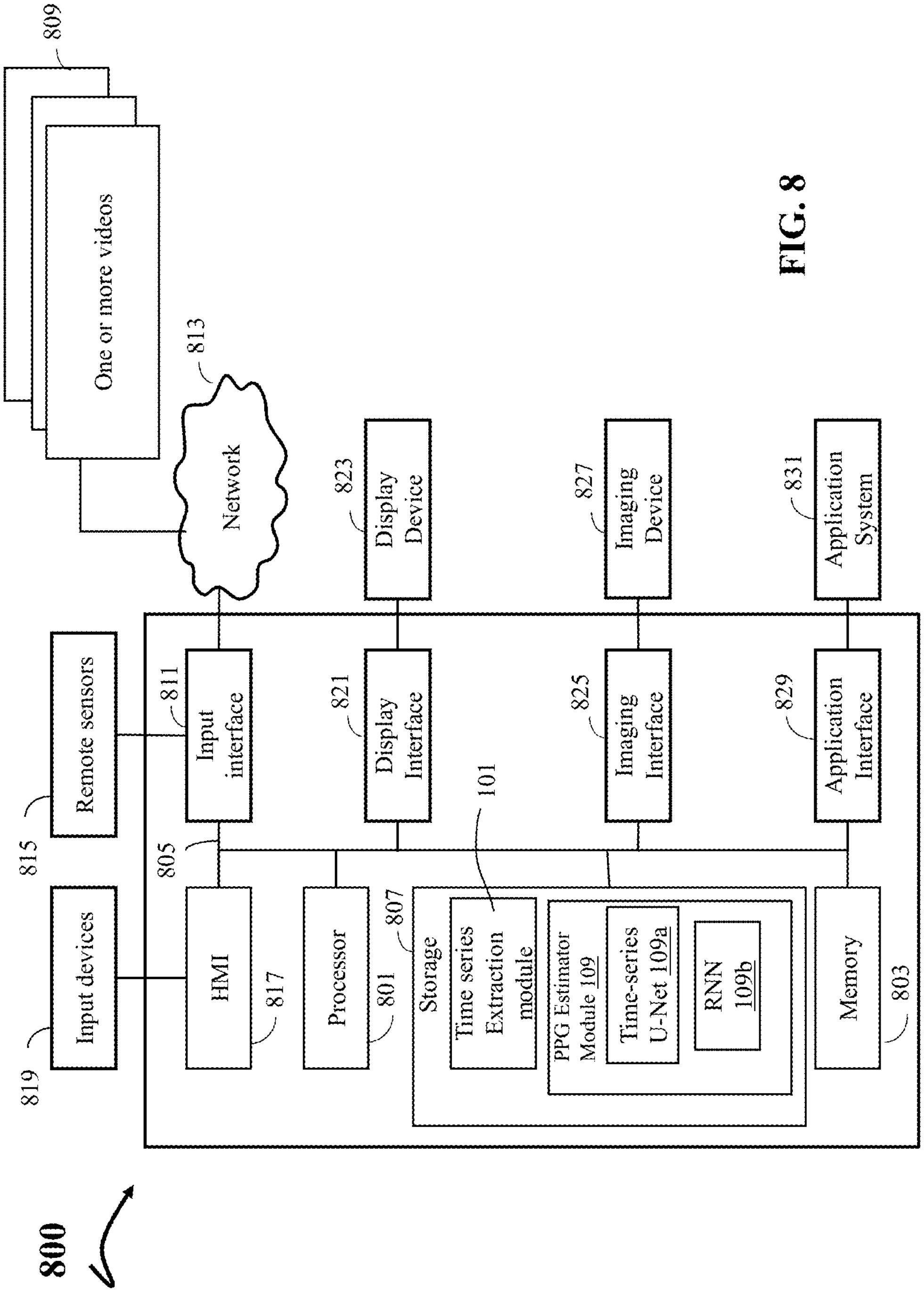
FIG. 8 illustrates a block diagram of the iPPG system, according to an example embodiment.

FIG. 8 illustrates a block diagram of the iPPG system 800, according to an example embodiment. The system 800 includes a processor 801 configured to execute stored instructions, as well as a memory 803 that stores instructions that are executable by the processor 801. The processor 801 can be a single core processor, a multi-core processor, a computing cluster, or any number of other configurations. The memory 803 can include random access memory (RAM), read only memory (ROM), flash memory, or any other suitable memory systems. The processor 801 is connected through a bus 805 to one or more input and output devices.

The instructions stored in the memory 803 correspond to an iPPG method for estimating the vital signs of the person based on a set of iPPG signals' waveforms measured from different regions of a skin of a person. The iPPG system 800 may also include a storage device 807 configured to store various modules such as the time-series extraction module 101 and the PPG estimator module 109, where the PPG estimator module 109 comprises the time-series U-net 109*a* and RNN 109*b*. The aforesaid modules stored in the storage device 807 are executed by the processor 801 to perform the vital signs estimations. The vital sign corresponds to a pulse rate of the person or heart rate variability of the person. The storage device 807 can be implemented using a hard drive, an optical drive, a thumb drive, an array of drives, or any combinations thereof.

The time-series extraction module 101 obtains an image from each frame of a video from one or more videos 809 that are fed to the iPPG system 800, where the one or more video 809 comprises a video of a body part of a person whose vital signs are to be estimated. The one or more videos may be recorded by one or more cameras. The time-series extraction module 101 may partition the image from each frame into a plurality of spatial regions corresponding to ROI of the body part that are strong indicators of PPG signal, where the partitioning of the image into the plurality of spatial regions form a sequence of images of the body part. Each image comprises different region of a skin of the body part in the image. The sequence of images may be transformed into a multidimensional time-series signal. The multidimensional time-series signal is provided to the PPG estimator module 109. The PPG estimator module 109 uses the time-series U-net 109*a* and the RNN 109*b* to process the multidimensional time-series signal by temporally convoluting multidimensional time-series signal and the convoluted data is further processes sequentially by the RNN 109*b* to estimate the PPG waveform, where the PPG waveform is used to estimate the vital signs of the person.

The iPPG system 800 includes an input interface 811 to receive the one or more videos 809. For example, the input interface 811 may be a network interface controller adapted to connect the iPPG system 800 through the bus 805 to a network 813.

Additionally or alternatively, in some implementations, the iPPG system 800 is connected to a remote sensor 815, such as a camera, to collect the one or more videos 809. In some implementations, a human machine interface (HMI) 817 within the iPPG system 800 connects the iPPG system 800 to input devices 819, such as a keyboard, a mouse, trackball, touchpad, joystick, pointing stick, stylus, touch-screen, and among others.

The iPPG system 800 may be linked through the bus 805 to an output interface to render the PPG waveform. For example, the iPPG system 800 may include a display interface 821 adapted to connect the iPPG system 800 to a display device 823, wherein the display device 823 may include, but not limited to, a computer monitor, a projector, or mobile device.

The iPPG system 800 may also include and/or be connected to an imaging interface 825 adapted to connect the iPPG system 800 to an imaging device 827.

In some embodiments, the iPPG system 800 may be connected to an application interface 829 through the bus 805 adapted to connect the iPPG system 800 to an application system 831 that can be operated based on the estimated vital signals. In an exemplary scenario, the application system 831 is a patient monitoring system, which uses the vital signs of a patient. In another exemplary scenario, the application system 831 is a driver monitoring system, which uses the vital signs of a driver to determine if the driver can drive safely, e.g., whether the driver is drowsy or not.

Figure 9:
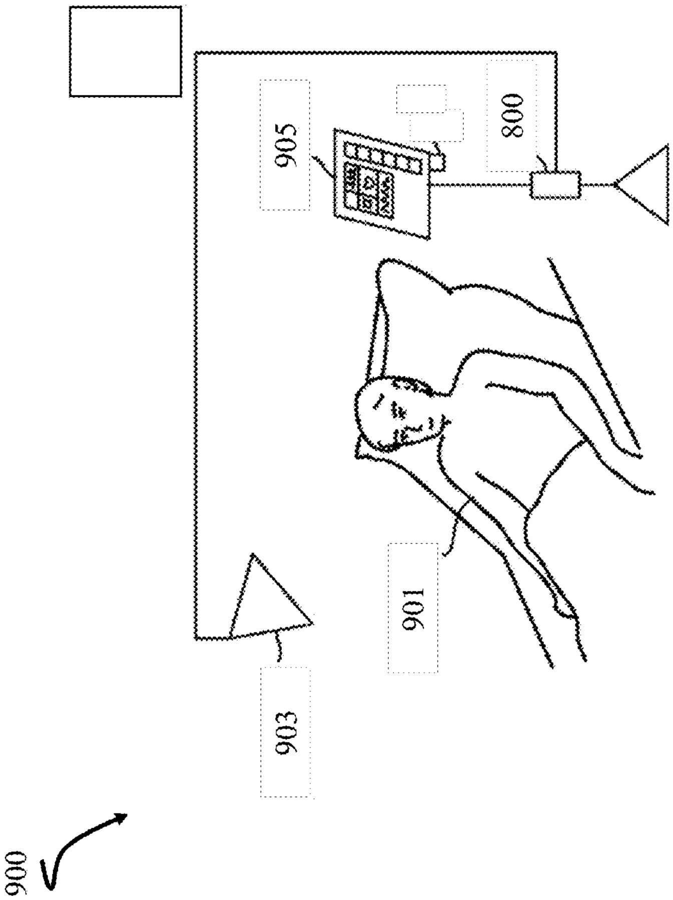
FIG. 9 illustrates a patient monitoring system using the iPPG system, according to an example embodiment.

FIG. 9 illustrates a patient monitoring system 900 using the iPPG system 800, according to an example embodiment. To monitor vital signs of the patient, a camera 903 is used to capture an image, i.e., a video sequence of the patient 901.

The camera 903 may include a CCD or CMOS sensor for converting incident light and the intensity variations thereof into an electrical signal. The camera 903 non-invasively captures light reflected from a skin portion of the patient 901. A skin portion may thereby particularly refer to the forehead, neck, wrist, part of the arm, or some other portion of the patient's skin. A light source, e.g., a near-infrared light source, may be used to illuminate the patient or a region of interest including a skin portion of the patient.

Based on the captured images, the iPPG system 800 determines the vital signs of the patient 901. In particular, the iPPG system 800 determines the vital signs such as the heart rate, the breathing rate or the blood oxygenation of the patient 901. Further, the determined vital signs are usually displayed on an operator interface 905 for presenting the determined vital signs. Such an operator interface 905 may be a patient bedside monitor or may also be a remote monitoring station in a dedicated room in a hospital, in a group care facility such as a nursing home, or even in a remote location in telemedicine applications.

Figure 10:
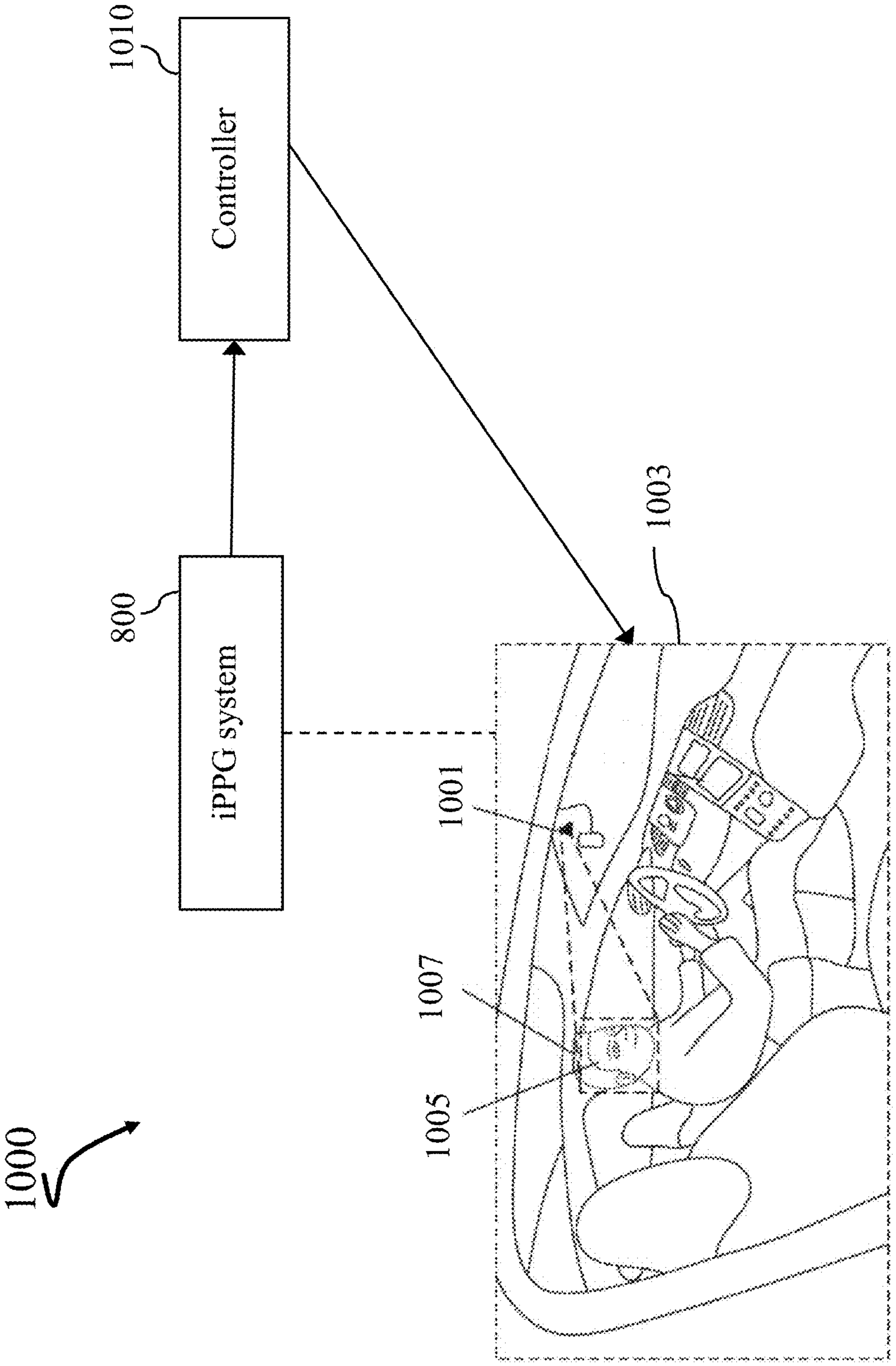
FIG. 10 illustrates a driver assistance system using the iPPG system, according to an example embodiment.

FIG. 10 illustrates a driver assistance system 1000 using the iPPG system 800, according to an example embodiment. The NIR light source and/or an NIR camera 1001 are arranged within a vehicle 1003. In particular, the NIR camera 1001 may be arranged in a field of view (FOV) 1007 capturing the driver 1005. The iPPG system 800 is integrated into the vehicle 1003. The NIR light source is configured to illuminate skin of a person driving the vehicle (driver 1005), and the NIR camera 1001 is configured to record the video of the driver in real time. Further, the NIR videos are fed to the iPPG system 800 to measure the iPPG signals from different regions of the skin of the driver 1005. The iPPG system 800 receives the measured iPPG signals and determines the vital sign, such as pulse rate, of the driver 1005.

Further, the processor of iPPG system 800 may produce one or more control action commands, based on the estimated vital signs of the driver 1005 of the vehicle 1003. The one or more control action commands includes vehicle braking, steering control, generation of an alert notification, initiation of an emergency service request, or switching of a driving mode. The one or more control action commands are transmitted to a controller 1010 of the vehicle 1003. The controller 1010 may control the vehicle 1003 according to one or more control action commands. For example, if the determined pulse rate of the driver is very low, then the driver 1005 may be experiencing a heart attack. Consequently, the iPPG system 800 may produce control commands for reducing a speed of the vehicle and/or steering control (e.g., to steer the vehicle to a shoulder of a highway and make it come to a halt) and/or initiate an emergency service request The above description provides exemplary embodiments only, and is not intended to limit the scope, applicability, or configuration of the disclosure. Rather, the above description of the exemplary embodiments will provide those skilled in the art with an enabling description for implementing one or more exemplary embodiments. Contemplated are various changes that may be made in the function and arrangement of elements without departing from the spirit and scope of the subject matter disclosed as set forth in the appended claims.

Specific details are given in the above description to provide a thorough understanding of the embodiments. However, it is understood by one of ordinary skill in the art that the embodiments may be practiced without these specific details. For example, systems, processes, and other elements in the subject matter disclosed may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

Also, individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed but may have additional steps not discussed or included in a figure. Furthermore, not all operations in any particularly described process may occur in all embodiments. A process may correspond to a method, a function, a procedure, a subroutine, a subprogram, etc. When a process corresponds to a function, the function's termination can correspond to a return of the function to the calling function or the main function.

Furthermore, embodiments of the subject matter disclosed may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

Various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine. Typically, the functionality of the program modules may be combined or distributed as desired in various embodiments.

Embodiments of the present disclosure may be embodied as a method, of which an example has been provided. The acts performed as part of the method may be ordered in any suitable way. Accordingly, embodiments may be constructed in which acts are performed in an order different than illustrated, which may include performing some acts concurrently, even though shown as sequential acts in illustrative embodiments. Although the present disclosure has been described with reference to certain preferred embodiments, it is to be understood that various other adaptations and modifications can be made within the spirit and scope of the present disclosure. Therefore, it is the aspect of the append claims to cover all such variations and modifications as come within the true spirit and scope of the present disclosure.

The invention claimed is:

1. An imaging photoplethysmography (iPPG) system for estimating a vital sign of a person from images of a skin of the person, comprising: at least one processor; and a memory having instructions stored thereon that, when executed by the at least one processor, cause the iPPG system to:

receive a sequence of images of different regions of the skin of the person, each region including pixels of different intensities indicative of variation of coloration of the skin;

transform the sequence of images into a multidimensional time-series signal, each dimension corresponding to a different region from the different regions of the skin;

process the multidimensional time-series signal with a time-series U-Net neural network to generate a PPG waveform, wherein a U-shape of the time-series U-Net neural network includes a contractive path that includes a sequence of contractive layers followed by an expansive path that includes a sequence of expansive layers, wherein at least some of the contractive layers downsample their input and at least some of the expansive layers upsample their input forming pairs of contractive and expansive layers of corresponding resolutions, wherein an output of each contractive layer of a plurality of contractive layers in the sequence of contractive layers is connected to (i.) a corresponding next contractive layer in the sequence of contractive layers and to (ii.) a corresponding expansive layer in the sequence of expansive layers via a corresponding pass through layer, wherein at least some of the corresponding contractive layers and expansive layers are connected through pass-through layers, wherein at least one of the pass-through layers includes a recurrent neural network that processes its input sequentially, and wherein the recurrent neural network is distinct from the contractive layers and expansive layers of the U-Net;

estimate the vital sign of the person based on the PPG waveform; and render the estimated vital sign of the person.

2. The iPPG system of claim 1, wherein at least one contractive layer from the sequence of contractive layers downsamples its input using a strided convolution with a stride greater than 1 to downsample and process the input.

3. The iPPG system of claim 1, wherein at least one expansive layer from the sequence of expansive layers upsamples its input with an up-convert operation to produce an upsampled input, and wherein the expansive layer includes multiple convolutional layers processing the upsampled input.

4. The iPPG system of claim 1, wherein the recurrent neural network includes a gated recurrent unit (GRU) or a long short-term memory (LSTM) network.

5. The iPPG system of claim 1, wherein to estimate the vital sign of the person from the PPG waveform, the at least one processor is configured to process, with the time-series U-Net neural network, each segment from a sequence of overlapping segments of the multidimensional time-series signal.

6. The iPPG system of claim 5, wherein a signal of the vital sign of the person is a one-dimensional signal.

7. The iPPG system of claim 1, wherein to produce the multidimensional time-series signal, the at least one processor is configured to identify the different regions of the skin of the person using a facial landmark detection; and average pixel intensities of pixels from each region of the different regions at an instant of time to produce a value for each dimension of the multidimensional time-series signal at the instant of time.

8. The iPPG system of claim 7, wherein each dimension of the multidimensional timeseries signal is a signal corresponding to the corresponding region of the different regions of the skin, wherein each region is an explicitly tracked region of interest (ROI).

9. The iPPG system of claim 1, wherein to transform the sequence of images into a multidimensional time-series signal includes a concatenation operation that combines more than one multidimensional time series, each extracted from a different channel of a multi-channel video, into a single multidimensional time series that comprises the multidimensional time-series signal.

10. The iPPG system of claim 1, wherein to transform the sequence of images into a multidimensional time-series signal includes a linear combination that combines more than one multidimensional time series, each extracted from a different channel of a multichannel video, into a single multidimensional time series that comprises the multidimensional time-series signal.

11. The iPPG system of claim 1, wherein to transform the sequence of images into a multidimensional time-series signal includes extracting more than one multidimensional time series, each extracted from one channel of a multichannel video, and shaping the more than one multidimensional time series into a 3D array that comprises the multidimensional time-series signal.

12. The iPPG system of claim 1, wherein the time-series U-net neural network is trained to maximize a Pearson correlation coefficient between ground truth data associated with the PPG waveform and the estimated PPG signal.

13. The iPPG system of claim 1, wherein the time-series U-net neural network is trained with a temporal loss function or a spectral loss function.

14. The iPPG system of claim 1, wherein the vital sign is one or a combination of a pulse rate of the person and a heart rate variability of the person.

15. The iPPG system of claim 1, wherein the person corresponds to a driver of a vehicle, and wherein the at least one processor is further configured to produce one or more control commands for a controller of the vehicle based on the vital sign of the driver.

16. The iPPG system of claim 15, further comprising: a controller configured to execute a control action based on the signal of the vital sign of the person.

17. The iPPG system of claim 1, further comprising:

a camera including a processor configured to measure the intensities indicative of variation of coloration of the skin at different instants of time to produce the sequence of images, a display device configured to display the signal of the vital sign of the person.

18. A method for estimating a vital sign of a person, wherein the method uses a processor coupled with stored instructions implementing the method, wherein the instructions, when executed by the processor carry out steps of the method, comprising:

receiving a sequence of images of different regions of the skin of the person, each region including pixels of different intensities indicative of variation of coloration of the skin;

transforming the sequence of images into a multidimensional time-series signal, each dimension corresponding to a different region from the different regions of the skin;

processing the multidimensional time-series signal with a time-series U-Net neural network to generate a PPG waveform, wherein a U-shape of the time-series U-Net neural network includes a contractive path that includes a sequence of contractive layers followed by an expansive path that includes a sequence of expansive layers, wherein at least some of the contractive layers downsample their input and at least some of the expansive layers upsample their input forming pairs of contractive and expansive layers of corresponding resolutions, wherein an output of each contractive layer of a plurality of layers of the sequence of contractive layers is connected to (i.) a corresponding next contractive layer in the sequence of contractive layers and to (ii.) a corresponding expansive layer in the sequence of expansive layers via a corresponding pass through layer, wherein at least some of the corresponding contractive layers and expansive layers are connected through pass-through layers, wherein at least one of the pass-through layers includes a recurrent neural network that processes its input sequentially, and wherein the recurrent neural network is distinct from the contractive layers and expansive layers of the U-Net;

estimating the vital sign of the person based on the PPG waveform; and rendering the estimated vital sign of the person.

19. A non-transitory computer-readable storage medium embodied thereon a program executable by a processor for performing a method, the method comprising:

receiving a sequence of images of different regions of the skin of the person, each region including pixels of different intensities indicative of variation of coloration of the skin;

transforming the sequence of images into a multidimensional time-series signal, each dimension corresponding to a different region from the different regions of the skin;

processing the multidimensional time-series signal with a time-series U-Net neural network to generate a PPG waveform, wherein a U-shape of the time-series U-Net neural network includes a contractive path that includes a sequence of contractive layers followed by an expansive path that includes a sequence of expansive layers, wherein at least some of the contractive layers downsample their input and at least some of the expansive layers upsample their input forming pairs of contractive and expansive layers of corresponding resolutions, where an output of each contractive layer of a plurality of contractive layers in the sequence of contractive layers is connected to (i.) a corresponding next contractive layer in the sequence of contractive layers and to (ii.) a corresponding expansive layer in the sequence of expansive layers via a corresponding pass through layer, wherein one or more contractive layers of the sequence of contractive layers comprise one or more of a convolutional layer, a single downsampling convolutional layer, and a dropout layer, wherein at least one of the pass-through layers includes a recurrent neural network that processes its input sequentially, and wherein the recurrent neural network is distinct from the contractive layers and expansive layers of the U-Net;

estimating the vital sign of the person based on the PPG waveform; and rendering the estimated vital sign of the person.

* * * * *